(12) United States Patent
Stevenson et al.

(10) Patent No.: US 9,889,306 B2
(45) Date of Patent: Feb. 13, 2018

(54) HERMETICALLY SEALED FEEDTHROUGH WITH CO-FIRED FILLED VIA AND CONDUCTIVE INSERT FOR AN ACTIVE IMPLANTABLE MEDICAL DEVICE

(71) Applicant: Greatbatch Ltd., Clarence, NY (US)

(72) Inventors: Robert A. Stevenson, Canyon Country, CA (US); Xiaohong Tang, Williamsville, NY (US); William C. Thiebolt, Tonawanda, NY (US); Christine A. Frysz, Orchard Park, NY (US); Keith W. Seitz, Clarence Center, NY (US); Richard L. Brendel, Carson City, NV (US); Thomas Marzano, East Amherst, NY (US); Jason Woods, Carson City, NV (US); Dominick J. Frustaci, Williamsville, NY (US); Steven W. Winn, Lancaster, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/797,123

(22) Filed: Jul. 11, 2015

(65) Prior Publication Data
US 2015/0314131 A1 Nov. 5, 2015

Related U.S. Application Data

(60) Continuation-in-part of application No. 14/182,569, filed on Feb. 18, 2014, which is a division of application No. 13/743,254, filed on Jan. 16, 2013, now Pat. No. 8,653,384.

(60) Provisional application No. 61/587,029, filed on Jan. 16, 2012, provisional application No. 61/587,287, filed on Jan. 17, 2012, provisional application No. 61/587,373, filed on Jan. 17, 2012.

(51) Int. Cl.
| | |
|---|---|
| *B01J 20/34* | (2006.01) |
| *A61N 1/375* | (2006.01) |
| *A61N 1/05* | (2006.01) |
| *H01G 2/10* | (2006.01) |
| *H01G 4/35* | (2006.01) |
| *H01R 43/00* | (2006.01) |
| *A61N 1/372* | (2006.01) |
| *C22C 29/12* | (2006.01) |

(52) U.S. Cl.
CPC ............ *A61N 1/3754* (2013.01); *A61N 1/05* (2013.01); *H01G 2/103* (2013.01); *H01G 4/35* (2013.01); *H01R 43/00* (2013.01); *A61N 1/372* (2013.01); *A61N 1/375* (2013.01); *B22F 2998/10* (2013.01); *C22C 29/12* (2013.01); *Y10T 156/1052* (2015.01)

(58) Field of Classification Search
CPC ................. C01B 31/088; B01J 20/34
USPC .......................................... 502/56
See application file for complete search history.

(56) References Cited

U.S. PATENT DOCUMENTS

| | | | |
|---|---|---|---|
| 3,137,808 | A | 6/1964 | Code et al. |
| 3,189,978 | A | 6/1965 | Stetson |
| 3,617,830 | A | 11/1971 | Perna, Jr. |
| 4,424,551 | A | 1/1984 | Stevenson et al. |
| 5,272,283 | A | 12/1993 | Kuzma |
| 5,333,095 | A | 7/1994 | Stevenson et al. |
| 5,406,444 | A | 4/1995 | Selfried et al. |
| 5,434,358 | A | 7/1995 | Glahn et al. |
| 5,470,345 | A | 11/1995 | Hassler et al. |
| 5,620,476 | A | 4/1997 | Truex et al. |
| 5,623,724 | A | 4/1997 | Gurkovich et al. |
| 5,650,759 | A | 7/1997 | Hittman et al. |
| 5,700,548 | A | 12/1997 | Warnier et al. |
| 5,735,884 | A | 4/1998 | Thompson et al. |
| 5,751,539 | A | 5/1998 | Stevenson et al. |
| 5,782,891 | A † | 7/1998 | Hassler |
| 5,855,995 | A | 1/1999 | Haq et al. |
| 5,896,267 | A | 4/1999 | Hittman et al. |
| 5,959,829 | A | 9/1999 | Stevenson et al. |
| 6,008,980 | A | 12/1999 | Stevenson et al. |
| 6,041,496 | A | 3/2000 | Haq et al. |
| 6,146,743 | A | 11/2000 | Haq et al. |
| 6,252,761 | B1 | 6/2001 | Branchevsky |

(Continued)

FOREIGN PATENT DOCUMENTS

| | | |
|---|---|---|
| EP | 0697725 | 2/1996 |
| EP | 2392382 | 7/2011 |

OTHER PUBLICATIONS

Lu, et al., Pt—Al2O3 interfacial bonding in implantable hermetic feedthroughs: Morphology and orientation, Society for Biomaterial—2011 Wiley Periodicals, Inc., Dec. 24, 2011, 817-824.

(Continued)

*Primary Examiner* — Edward Johnson
(74) *Attorney, Agent, or Firm* — Michael F. Scalise

(57) ABSTRACT

A hermetically sealed feedthrough for attachment to an active implantable medical device includes a dielectric substrate configured to be hermetically sealed to a ferrule or an AIMD housing. A via hole is disposed through the dielectric substrate from a body fluid side to a device side. A conductive fill is disposed within the via hole forming a filled via electrically conductive between the body fluid side and the device side. A conductive insert is at least partially disposed within the conductive fill. Then, the conductive fill and the conductive insert are co-fired with the dielectric substrate to form a hermetically sealed and electrically conductive pathway through the dielectric substrate between the body fluid side and the device side.

36 Claims, 33 Drawing Sheets

(56) References Cited

U.S. PATENT DOCUMENTS

| | | |
|---|---|---|
| 6,284,080 B1 | 9/2001 | Haq et al. |
| 6,414,835 B1 † | 7/2002 | Wolf |
| 6,456,481 B1 | 9/2002 | Stevenson |
| 6,470,545 B1 | 10/2002 | Branchevsky |
| 6,660,116 B2 | 12/2003 | Wolf et al. |
| 6,694,583 B2 | 2/2004 | Branchevsky |
| 6,812,404 B1 | 11/2004 | Martinez |
| 7,035,076 B1 | 4/2006 | Stevenson |
| 7,064,270 B2 | 6/2006 | Marshall et al. |
| 7,068,491 B1 | 6/2006 | Burdon et al. |
| 7,145,076 B2 | 12/2006 | Knappen et al. |
| 7,164,572 B1 | 1/2007 | Burdon et al. |
| 7,310,216 B2 | 12/2007 | Stevenson et al. |
| 7,480,988 B2 | 1/2009 | Ok et al. |
| 7,693,576 B1 | 4/2010 | Lavie et al. |
| 7,719,854 B2 | 5/2010 | Youker et al. |
| 7,812,691 B1 | 10/2010 | Fisk et al. |
| 7,901,761 B1 | 3/2011 | Jiang et al. |
| 7,957,806 B2 | 6/2011 | Stevenson et al. |
| 7,989,080 B2 | 8/2011 | Greenberg et al. |
| 8,000,804 B1 | 8/2011 | Wessendorf et al. |
| 8,043,454 B1 | 10/2011 | Jiang et al. |
| 8,163,397 B2 | 4/2012 | Ok et al. |
| 8,536,468 B2 | 9/2013 | Teske |
| 8,653,384 B2 | 2/2014 | Marzano et al. |
| 8,938,309 B2 | 1/2015 | Marzano et al. |
| 9,233,253 B2 | 1/2016 | Stevenson et al. |
| 2002/0027282 A1 | 3/2002 | Kawakami et al. |
| 2002/0139556 A1 | 10/2002 | Ok et al. |
| 2003/0213605 A1 | 11/2003 | Brendel et al. |
| 2005/0190527 A1 | 9/2005 | Stevenson et al. |
| 2005/0195556 A1 | 9/2005 | Shah |
| 2006/0259093 A1 | 11/2006 | Stevenson et al. |
| 2007/0060969 A1 | 3/2007 | Burdon et al. |
| 2007/0060970 A1 | 3/2007 | Burdon et al. |
| 2007/0236861 A1 | 10/2007 | Burdon et al. |
| 2008/0314502 A1 | 12/2008 | Ok et al. |
| 2009/0243756 A1 | 10/2009 | Stevenson et al. |
| 2009/0259265 A1 | 10/2009 | Stevenson et al. |
| 2010/0023086 A1 | 1/2010 | Lim |
| 2010/0160991 A1 | 6/2010 | Lim |
| 2011/0000699 A1 | 1/2011 | Bealka et al. |
| 2011/0034965 A1 | 2/2011 | Troetzschel et al. |
| 2011/0048770 A1 † | 3/2011 | Reiterer et al. |
| 2011/0048990 A1 | 3/2011 | Goda |
| 2011/0106205 A1 | 5/2011 | Reiterer et al. |
| 2011/0248184 A1 | 10/2011 | Shah |
| 2012/0193117 A1 | 8/2012 | Specht et al. |
| 2012/0197327 A1 | 8/2012 | Specht |

OTHER PUBLICATIONS

European Search Report for 13151535.5 dated Jul. 2, 2013.
European Search Report for 13151536 dated Jun. 13, 2013.
European Search Report for 13151537.1 dated Jul. 11, 2013.
European Search Report for 13151537.1 dated Jun. 26, 2013.

† cited by third party

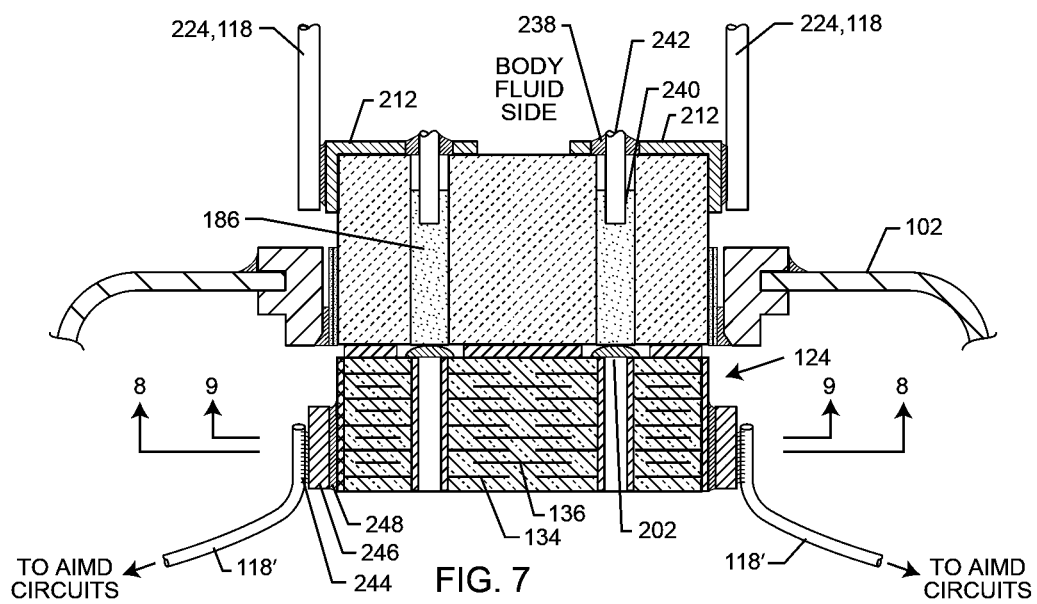
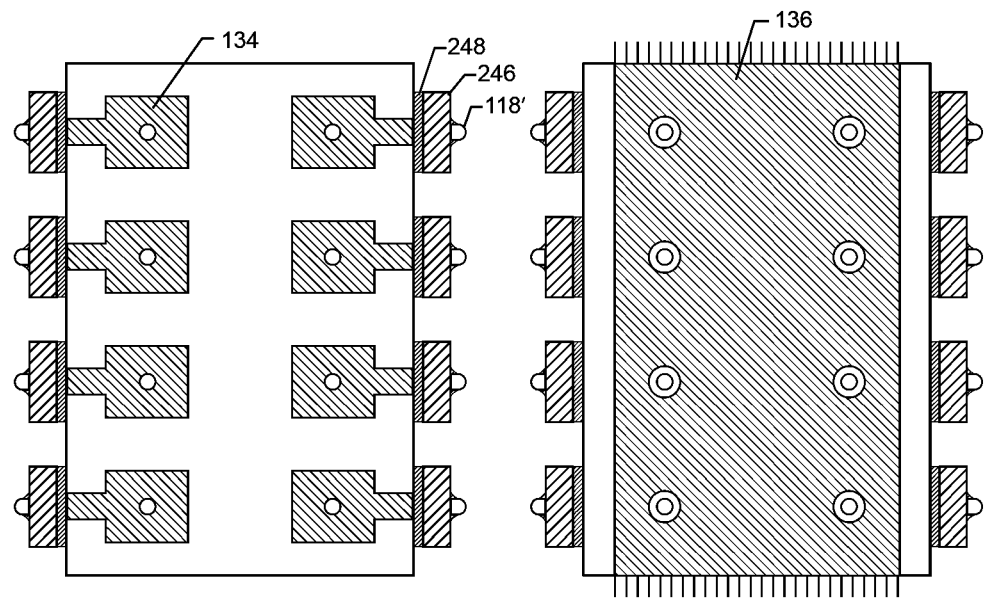
FIG. 7
FIG. 8
FIG. 9

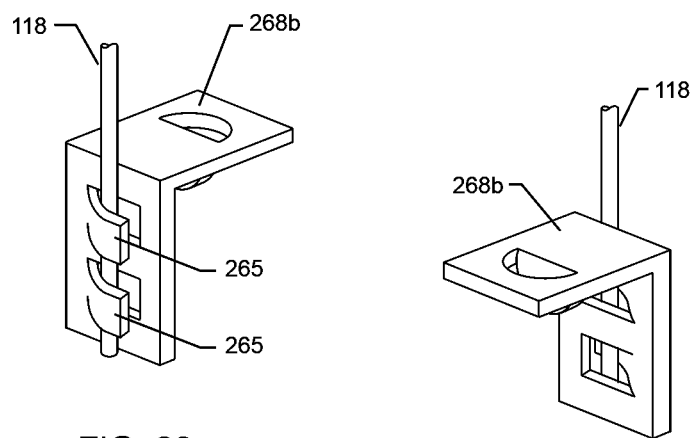
FIG. 20
FIG. 21
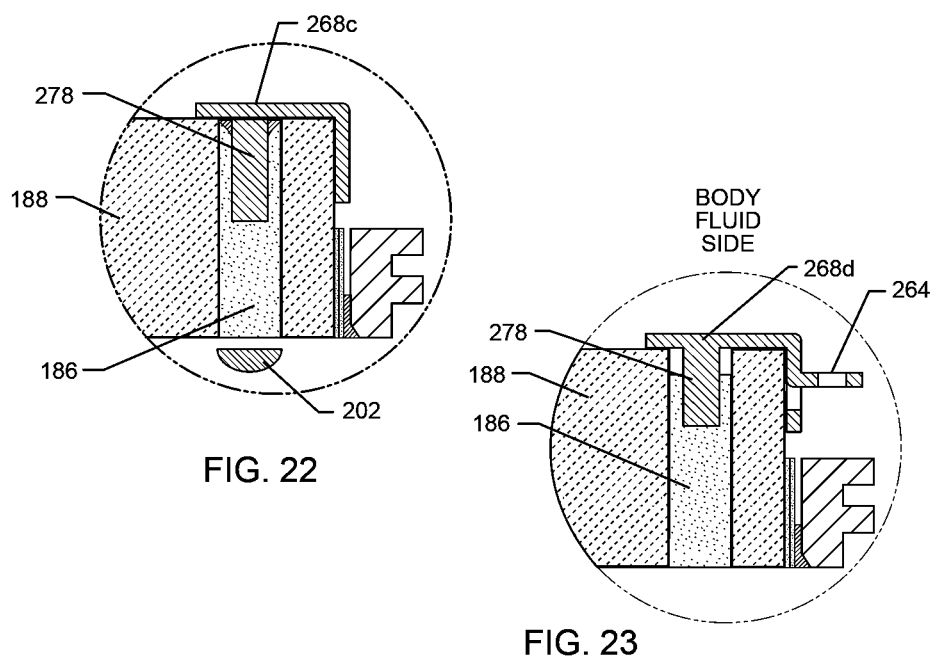
FIG. 22
FIG. 23

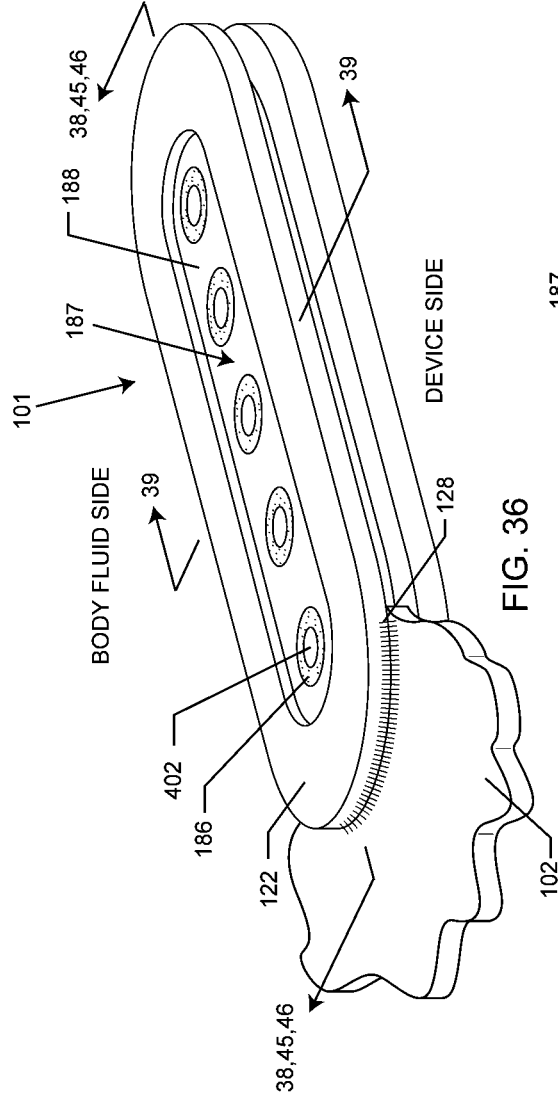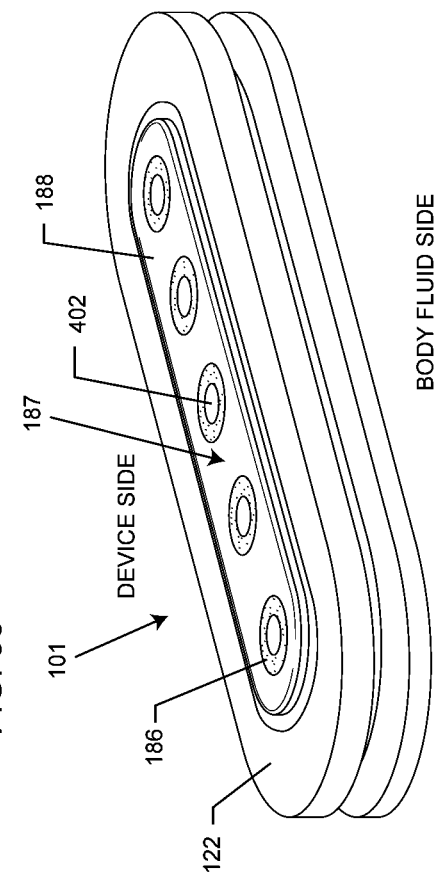

FIG. 61 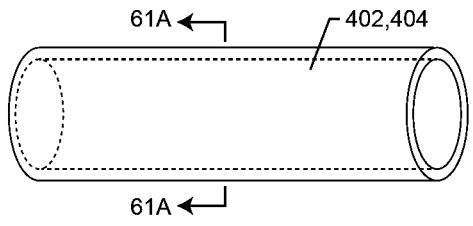 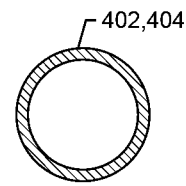
FIG. 61A
FIG. 62 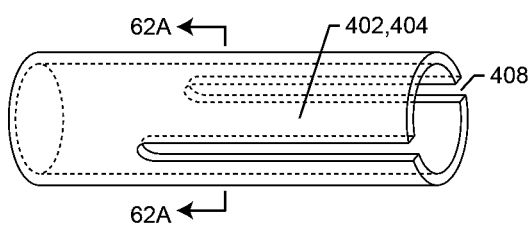 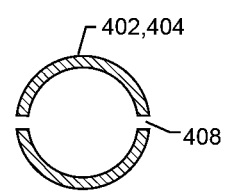
FIG. 62A
FIG. 63 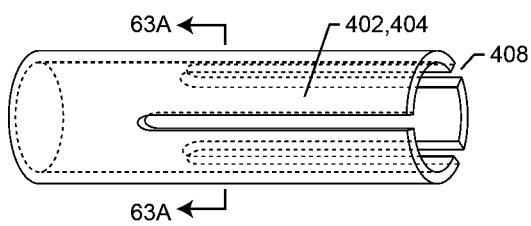 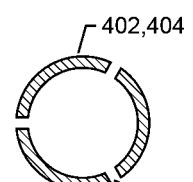
FIG. 63A
FIG. 64 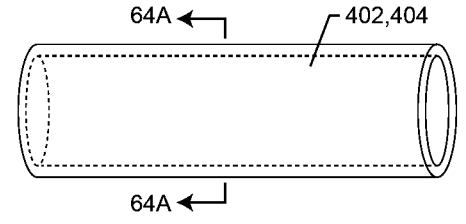 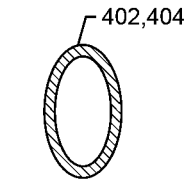
FIG. 64A
FIG. 65 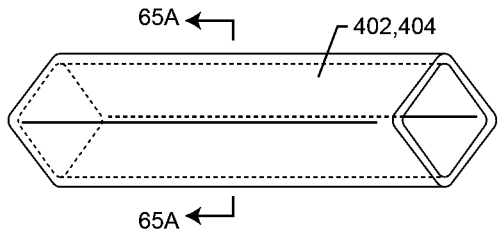 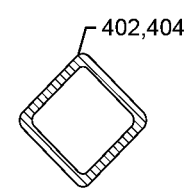
FIG. 65A

HERMETICALLY SEALED FEEDTHROUGH WITH CO-FIRED FILLED VIA AND CONDUCTIVE INSERT FOR AN ACTIVE IMPLANTABLE MEDICAL DEVICE

CROSS-REFERENCE TO RELATED APPLICATIONS

This is a continuation-in-part application of application Ser. No. 14/182,569 filed on Feb. 18, 2014, which itself was a division of application Ser. No. 13/743,254 filed on Jan. 16, 2013 and now U.S. Pat. No. 8,653,384 issued on Feb. 18, 2014, which itself claimed priority to three provisional applications which are U.S. Application Ser. Nos. 61/587,029, filed on Jan. 16, 2012; 61/587,287, filed on Jan. 17, 2012; and 61/587,373, filed on Jan. 17, 2012. The contents of all the above mentioned applications are herein incorporated in full with these references.

DESCRIPTION

Field of the Invention

The present invention generally relates to implantable medical devices and hermetic terminal subassemblies. More particularly, the present invention relates to a hermetic terminal subassembly utilizing a co-fired essentially pure platinum filled via along with novel ways of making electrical connections on the body fluid and device side of the active implantable medical device (AIMD) housing.

Background of the Invention

A wide assortment of active implantable medical devices (AIMD) are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue.

The hermetic terminal or feedthrough of these implantable devices is considered critical. Hermetic terminals or feedthroughs are generally well-known in the art for connecting electrical signals through the housing or case of an AIMD. For example, in implantable medical devices such as cardiac pacemakers, implantable cardioverter defibrillators, and the like, a hermetic terminal comprises one or more conductive terminal pins supported by an insulative structure for feedthrough passage from the exterior to the interior of an AIMD electromagnetic shield housing. Hermetic terminals or feedthroughs for AIMDs must be biocompatible as well as resistant to degradation under applied bias current or voltage. Hermeticity of the feedthrough is imparted by judicious material selection and carefully prescribed manufacturing processing. Sustainable hermeticity of the feedthrough over the lifetime of these implantable devices is critical because the hermetic terminal intentionally isolates the internal circuitry and components of the device from the external environment to which the component is exposed. In particular, the hermetic terminal isolates the internal circuitry, connections, power sources and other components in the device from ingress of body fluids. Ingress of body fluids into an implantable medical device is known to be a contributing factor to device malfunction and may contribute to the compromise or failure of electrical circuitry, connections, power sources and other components within an implantable medical device that are necessary for consistent and reliable device therapy delivery to a patient. Furthermore, ingress of body fluids may compromise an implantable medical device's functionality which may constitute electrical shorting, element or joint corrosion, metal migration or other such harmful consequences affecting consistent and reliable device therapy delivery.

In addition to concerns relative to sustained terminal or feedthrough hermeticity, other potentially compromising conditions must be addressed, particularly when a hermetic terminal or feedthrough is incorporated within an implantable medical device. For example, the hermetic terminal or feedthrough pins are typically connected one or more leadwires of implantable therapy delivery leads. These implantable therapy delivery leads can effectively act as antennas of electromagnetic interference (EMI) signals. Therefore, when these electromagnetic signals enter within the interior space of a hermetic implantable medical device, facilitated by the therapy delivery leads, they can negatively impact the intended function of the medical device and as a result, negatively impact therapy delivery intended for a patient by that device. EMI engineers commonly refer to this as the "genie in the bottle" effect. In other words, once the genie (i.e., EMI) is inside the hermetic device, it can wreak havoc with electronic circuit functions by cross-coupling and re-radiating within the device.

Another particularly problematic condition associated with implanted therapy delivery leads occurs when a patient is in an MRI environment. In this case, the electrical currents imposed on the implanted therapy delivery leads can cause the leads to heat to the point where tissue damage is likely. Moreover, the electrical currents developed in these implanted therapy delivery leads during an MRI procedure can disrupt or damage the sensitive electronics within the implantable medical device.

Therefore, materials selection and fabrication processing parameters are of utmost importance in creating a hermetic terminal (or feedthrough) or a structure embodying a hermetic terminal (or feedthrough), that can survive anticipated and possibly catastrophically damaging environmental conditions and that can be practically and cost effectively manufactured.

Hermetic terminals or feedthrough assemblies utilizing ceramic dielectric materials may fail in a brittle manner. A brittle failure typically occurs when the ceramic structure is deformed elastically up to an intolerable stress, at which point the ceramic fails catastrophically. Virtually all brittle failures occur by crack propagation in a tensile stress field. Even microcracking caused by sufficiently high tensile stress concentrations may result in a catastrophic failure including loss of hermeticity identified as critical in hermetic terminals for implantable medical devices. Loss of hermeticity may be a result of design aspects such as a sharp corner which creates a stress riser, mating materials with a difference of coefficient of thermal expansions (CTE) that generate tensile stresses that ultimately result in loss of hermeticity of the feedthrough or interconnect structure.

In the specific case of hermetic terminal or feedthrough designs, a tensile stress limit for a given ceramic based hermetic design structure cannot be specified because failure stress in these structures is not a constant. As indicated above, variables affecting stress levels include the design itself, the materials selection, symmetry of the feedthrough, and the bonding characteristics of mating surfaces within the feedthrough. Hence, length, width and height of the overall ceramic structure matters as do the number, spacing, length and diameter of the vias in that structure. The selection of the mating materials, that is, the material that fills the vias and the material that forms the base ceramic, are important. Finally, the fabrication processing parameters, particularly at binder burnout, sintering and cool down, make a difference. When high reliability is required in an application such as indicated with hermetic terminals or feedthroughs for AIMDs, to provide ensurance for a very low probability of failure it is necessary to design a hermetic terminal assembly or feedthrough structure so that stresses imparted by design, materials and/or processing are limited to a smaller level of an average possible failure stress. Further, to provide ensurance for a very low probability of failure in a critical ceramic based assembly or subassembly having sustainable hermetic requirements, it is also necessary to design structures embodying a hermetic terminal or feedthrough such that stresses in the final assembly or subassembly are limited to a smaller level of an average possible failure stress for the entire assembly or subassembly. In hermetic terminals and structures comprising hermetic terminals for AIMDs wherein the demand for biocompatibility exists, this task becomes even more difficult.

The most critical feature of a feedthrough design or any terminal subassembly is the metal/ceramic interface within the feedthrough that establishes the hermetic seal. The present invention therefore, provides a hermetic feedthrough comprising a monolithic alumina insulator substrate within which a platinum conductive pathway or via resides. More specifically, the present invention provides a hermetic feedthrough in which the hermetic seal is created through the intimate bonding of the platinum metal residing within the alumina substrate.

A traditional ceramic-to-metal hermetic terminal is an assembly of three components: metal leadwires that conduct electrical current, a ceramic insulator, and a metal housing, which is referred to as the flange or the ferrule. Brazed joints hermetically seal the metal leadwires and the flange or ferrule to the ceramic insulator. For a braze-bonded joint, the braze material is generally intended to deform in a ductile manner in order to compensate for perturbations that stress the bond between the mating materials as the braze material may provide ductile strain relief when the thermal expansion mismatch between the ceramic and metal is large. Thus, mating materials with large mismatches in CTE can be coupled through braze materials whose high creep rate and low yield strength reduce the stresses generated by the differential contraction existing between these mating materials.

Thermal expansion of metal is generally considerably greater than those of ceramics. Hence, successfully creating a hermetic structure, and one that can sustain its hermeticity in service, is challenging due to the level of residual stresses in the final structure. Specifically, thermal expansion mismatch results in stresses acting along the ceramic/metal interface that tend to separate the ceramic from the metal and so the bond developed between the ceramic and the metal must be of sufficient strength to withstand these stresses, otherwise adherence failure, that is, loss of hermeticity, will occur. One method for limiting these stresses is to select combinations of materials whose thermal contractions after bonding are matched.

In making the selection for a CTE match, it is important to note that very few pairs of materials have essentially identical thermal expansion curves. Generally, the metal component is selected first based on electrical and thermal conductivity, thermal expansion, ability to be welded or soldered, mechanical strength, and chemical resistance or biocompatibility requirements; the ceramic is then selected based primarily on electrical resistivity, dielectric strength, low gas permeability, environmental stability, and thermal expansion characteristics. In the specific case of selecting platinum wire, often the ceramic formulation is modified in order to match its CTE to that of the platinum wire. In yet a more specific case of selecting platinum paste, the platinum paste formulation may be modified as well. If the mating materials are alumina of at least 96% purity and essentially pure platinum paste, then matching CTE is not possible. Thus, for AIMD's, consistently achieving hermetic terminal structures that are capable of sustaining hermeticity throughout the application's service life has proven challenging.

Producing a stress-free structure often not only involves bonding a pair of materials but also achieving that bond at a very specific temperature so that their contractions on cooling to room temperature are essentially the same even though the contraction curves may not coincide. Since this often is a significant challenge, hermetic terminals are produced by metalizing the alumina and using a brazing material to form the bond at some other temperature than an intersection of the CTE curves. (NOTE: Forming a bond between two materials that become rigid at the intersection of the two CTE curves makes it possible to produce a structure that is stress free at room temperature, unless the two CTE curves separate substantially from each other from the intersection point and room temperature.) The deformation of the braze material by time-independent plastic flow or creep relaxation limits the stresses generated in the ceramic. Given this, the impact of the rate of cooling on the final stress level of a structure must also be considered. In some cases, residual stresses are generated deliberately to provide protective compressive stresses in the ceramic part and in the bond interface. Usually this is accomplished by selecting components with different CTEs. Another way is to control the shrinkage of one material over its mating material. In either case, it is important to minimize stress levels such that the interface on which hermeticity depends is well within the stress level at which failure might occur.

In an embodiment, the present invention is directed to mating bound particulate high purity alumina of at least 96% and particles of essentially pure platinum metal that are suspended within a mixture of solvents and binders, i.e. a platinum paste. This combination of materials does not use a braze material to buffer the CTE mismatch between these two materials. Further, since the intent of this invention is to provide hermetic terminals and subassemblies comprising hermetic terminals for AIMDs, the present invention does not consider modifications to the alumina formulation or the platinum paste in an attempt to match their CTEs. Rather, this invention discloses sustainable hermetic terminals and structures embodying these hermetic terminals. This is achieved by adjusting platinum paste solids loading, prescribing via packing, prescribing binder burnout, sintering and cool down parameters, such that shrinkage of the alumina is greater than the shrinkage of the platinum fill in the via and an intimate and tortuous (a mutually conformal) interface is created that may be a direct bond between the alumina and platinum materials that is hermetic. Alternatively, or that may develop an amorphous interfacial layer that is not susceptible to erosion by body fluids and can tolerate stress levels without losing hermeticity.

Regarding EMI, a terminal or feedthrough capacitor EMI filter may be disposed at, near or within a hermetic terminal or feedthrough resulting in a feedthrough filter capacitor which diverts high frequency electrical signals from lead conductors to the housing or case of an AIMD. Many different insulator structures and related mounting methods are known in the art for use of feedthrough capacitor EMI filters in AIMDs, wherein the insulative structure also provides a hermetic terminal or feedthrough to prevent entry of body fluids into the housing of an AIMD. In the prior art devices, the hermetic terminal subassembly has been combined in various ways with a ceramic feedthrough filter EMI capacitor to decouple interference signals to the housing of the medical device.

In a typical prior art unipolar construction (as described in U.S. Pat. No. 5,333,095 and herein incorporated by reference), a round/discoidal (or rectangular) ceramic feedthrough EMI filter capacitor is combined with a hermetic terminal pin assembly to suppress and decouple undesired interference or noise transmission along a terminal pin. The feedthrough capacitor is coaxial having two sets of electrode plates embedded in spaced relation within an insulative dielectric substrate or base, formed typically as a ceramic monolithic structure. One set of the electrode plates are electrically connected at an inner diameter cylindrical surface of the coaxial capacitor structure to the conductive terminal pin utilized to pass the desired electrical signal or signals. The other or second set of electrode plates are coupled at an outer diameter surface of the round/discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the coaxial capacitor. The outer feedthrough capacitor electrode plate sets (or "ground" plates) are coupled in parallel together by a metalized layer which is either fired, sputtered or plated onto the ceramic capacitor. This metalized band, in turn, is coupled to the ferrule by conductive adhesive, soldering, brazing, welding, or the like. The inner feedthrough capacitor electrode plate sets (or "active" plates) are coupled in parallel together by a metalized layer which is either glass frit fired or plated onto the ceramic capacitor. This metalized band, in turn, is mechanically and electrically coupled to the lead wire(s) by conductive adhesive, soldering, or the like. In operation, the coaxial capacitor permits passage of relatively low frequency biologic signals along the terminal pin, while shielding and decoupling/attenuating undesired interference signals of typically high frequency to the AIMD conductive housing. Feedthrough capacitors of this general type are available in unipolar (one), bipolar (two), tripolar (three), quadpolar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the ferrule of the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

Regarding MRI related issues, bandstop filters, such as those described in U.S. Pat. No. 6,008,980, which is herein incorporated by reference, reduce or eliminate the transmission of damaging frequencies along the leads while allowing the desired biologic frequencies to pass efficiently through.

Referring once again to feedthrough capacitor EMI filter assemblies, although these assemblies as described earlier have performed in a generally satisfactory manner, and notwithstanding that the associated manufacturing and assembly costs are unacceptably high in that the choice of the dielectric material for the capacitor has significant impacts on cost and final performance of the feedthrough filter capacitor, alumina ceramic has not been used in the past as the dielectric material for AIMD feedthrough capacitors. Alumina ceramic is structurally strong and biocompatible with body fluids but has a dielectric constant around 6 (less than 10). There are other more effective dielectric materials available for use in feedthrough filter capacitor designs. Relatively high dielectric constant materials (for example, barium titanate with a dielectric constant of over 2,000) are traditionally used to manufacture AIMD feedthrough capacitors for integrated ceramic capacitors and hermetic seals resulting in more effective capacitor designs. Yet ceramic dielectric materials such as barium titanate are not as strong as the alumina ceramic typically used to manufacture the hermetic seal subassembly in the prior art. Barium titanate is also not biocompatible with body fluids. Direct assembly of the ceramic capacitor can result in intolerable stress levels to the capacitor due to the mismatch in thermal coefficients of expansion between the titanium pacemaker housing (or other metallic structures) and the capacitor dielectric. Hence, particular care must be used to avoid cracking of the capacitor element. Accordingly, the use of dielectric materials with a low dielectric constant and a relatively high modulus of toughness are desirable yet still difficult to achieve for capacitance-efficient designs.

Therefore, it is very common in the prior art to construct a hermetic terminal subassembly with a feedthrough capacitor attached near the inside of the AIMD housing on the device side. The feedthrough capacitor does not have to be made from biocompatible materials because it is located on the device side inside the AIMD housing. The hermetic terminal subassembly allows leadwires to hermetically pass through the insulator in non-conductive relation with the ferrule or the AIMD housing. The leadwires also pass through the feedthrough capacitor to the inside of the AIMD housing. These leadwires are typically continuous and must be biocompatible and non-toxic. Generally, these leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material stiffness and to enable the hermetic terminal subassembly leadwire to sustain bending stresses. An issue with the use of platinum for leadwires is that platinum has become extremely expensive and may be subject to premature fracture under rigorous processing such as ultrasonic cleaning or application use/misuse, possibly unintentional damaging forces resulting from Twiddler's Syndrome.

Accordingly, what is needed is a filtered structure like a hermetic terminal or feedthrough, any subassembly made using same and any feedthrough filter EMI capacitor assembly which minimizes intolerable stress levels, allows use of preferred materials for AIMDS and eliminates high-priced, platinum, platinum-iridium or equivalent noble metal hermetic terminal subassembly leadwires. Also, what is needed is an efficient, simple and robust way to connect the leadwires in a header block to the novel hermetic terminal subassembly. Correspondingly, it is also needed to make a similar efficient, simple and robust electrical connection between the electronics on the device side of the AIMD to the feedthrough capacitor and hermetic terminal subassembly. The present invention fulfills these needs and provides other related advantages.

SUMMARY OF THE INVENTION

An exemplary embodiment of a hermetically sealed feedthrough for attachment to an active implantable medical device includes a dielectric substrate configured to be hermetically sealed to a ferrule or an AIMD housing. A via hole is disposed through the dielectric substrate from a body fluid side to a device side. A conductive fill is disposed within the via hole forming a filled via electrically conductive between the body fluid side and the device side. A conductive insert is at least partially disposed within the conductive fill. The conductive fill and the conductive insert are co-fired with the dielectric substrate to form a hermetically sealed and electrically conductive pathway through the dielectric substrate between the body fluid side and the device side.

In other exemplary embodiments the conductive fill may include a substantially closed pore and substantially pure metallic fill. The conductive insert may include a substantially pure metallic insert, where the metallic insert and the metallic fill are of the same metallic material type. An inherent shrink rate during a co-firing treatment of the dielectric substrate in a green state may be greater than that of an inherent shrink rate during the co-firing treatment of the metallic fill in a green state.

In other exemplary embodiments the conductive fill may include a substantially closed pore and substantially pure platinum fill. The conductive insert may include a substantially pure platinum insert. The dielectric substrate may include an alumina substrate comprised of at least 96 percent alumina. The hermetically sealed and electrically conductive pathway may include a first hermetic seal between the platinum fill and the alumina dielectric substrate, wherein the platinum fill forms a tortuous and mutually conformal knitline or interface between the alumina substrate and the platinum fill. The hermetically sealed and electrically conductive pathway may include a second hermetic seal between the platinum fill and the platinum insert, wherein the platinum fill forms a second tortuous and mutually conformal knitline or interface between the platinum fill and the platinum insert. At least a portion of an outer surface of the platinum insert may be forming the second tortuous and mutually conformal knitline or interface comprises a substantially irregular surface.

The conductive insert may be exposed through the conductive fill on the body fluid side or the device side of the dielectric substrate. The conductive insert may be flush with a device side surface or a body fluid side surface of the dielectric substrate. The conductive insert may extend beyond a device side surface or a body fluid side surface of the dielectric substrate. The conductive insert may include an enlarged end cap on the device side or the body fluid side of the dielectric substrate. The conductive insert may include a first portion separate and distinct from a second portion, where the first and second portions are configured to abut one another when disposed from opposite sides of the body fluid side and the device side through the conductive fill.

The conductive insert may include a crimp post extending beyond a device side surface or a body fluid side surface of the dielectric substrate. The crimp post may include a receptacle configured to receive a conductive wire, wherein the crimp post comprises a cross-sectional shape of a circle, an oval, a rectangle or a square. The crimp post may include at least one slot at least partially disposed along a longitudinal length of the crimp post. The at least one slot may be fully disposed along the longitudinal length of the crimp post.

A feedthrough capacitor may be disposed on the device side of the dielectric substrate, the feedthrough capacitor comprising at least one active electrode plate separated from at least one ground electrode plate by a capacitor dielectric, wherein the at least one active electrode plate is electrically coupled to the conductive pathway and wherein the at least one ground electric plate is electrically coupled to the ferrule or AIMD housing, wherein the feedthrough capacitor forms a frequency selective diverter circuit between the conductive pathway and to the ferrule or AIMD housing.

A circuit board may be disposed on the device side of the dielectric substrate, wherein the circuit board comprises at least one monolithic chip capacitor (MLCC) electrically coupled between the conductive pathway and to the ferrule or AIMD housing, where the MLCC forms a frequency selective diverter circuit between the conductive pathway and to the ferrule or AIMD housing.

A shielded three-terminal flat-through EMI energy dissipating filter may be disposed on the device side of the dielectric substrate, the flat-through filter comprising: i) at least one active electrode plate through which a circuit current is configured to pass between a first terminal and a second terminal; ii) at least one first shield plate disposed on a first side of the at least one active electrode plate; and iii) at least one second shield plate disposed on a second side of the at least one active electrode plate, where the at least one second shield plate is disposed opposite the at least one first shield plate; iv) wherein the at least one first and second shield plates are both electrically coupled to a third terminal, where the third terminal is configured to be electrically coupled directly or indirectly to the ferrule or the AIMD housing; v) wherein the conductive pathway is electrically coupled directly or indirectly to the at least one active electrode plate and where the conductive pathway is in non-conductive relationship to the at least one first and second shield plates, the ferrule and the AIMD housing.

The conductive insert may include titanium, platinum, platinum-iridium alloys, tantalum, niobium, zirconium, hafnium, nitinol, Co—Cr—Ni alloys, stainless steel, gold, gold alloys, ZrC, ZrN, TiN, NbO, TiC or TaC.

The receptacle of the crimp post may be disposed perpendicular to a longitudinal length of the crimp post. Alternatively, the receptacle of the crimp post may be aligned with a longitudinal length of the crimp post.

The conductive fill may have a larger cross-sectional area at the device side or body fluid side as compared to a center portion of the conductive fill.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 7 is a sectional view of another feedthrough assembly with a capacitor mounted on the device side;

FIG. 8 is a sectional view taken from FIG. 7 along lines 8-8 now showing the active plates;

FIG. 9 is a sectional view taken from FIG. 7 along lines 9-9 now showing the ground plates;

FIG. 20 is a perspective view of another embodiment of a wire bond pad with attachment fingers;

FIG. 21 is another perspective view of the embodiment of wire bond pad in FIG. 20;

FIG. 22 is an enlarged sectional view of another embodiment of a wire bond pad with a pin co-fired into the platinum filled via;

FIG. 23 is an enlarged sectional view of another embodiment of a wire bond pad similar to FIG. 55 now showing a hole to capture the leadwire;

FIG. 36 is a perspective view of a hermetic seal sub-assembly shown laser welded into an opening in the housing of an active implantable medical device;

FIG. 37 shows the device side of a hermetic terminal sub-assembly now shown on top;

FIG. 61 is a perspective view showing one embodiment of a crimp post;

FIG. 61A is a sectional view of the structure of FIG. 61 taken along lines 61A-61A;

FIG. 62 shows another embodiment of a crimp post with two slots;

FIG. 62A is a sectional view of the structure of FIG. 62 taken along lines 62A-62A;

FIG. 63 shows another embodiment of a crimp post with three slots;

FIG. 63A is a sectional view of the structure of FIG. 63 taken along lines 63A-63A;

FIG. 64 shows another embodiment of an oval crimp post;

FIG. 64A is a sectional view of the structure of FIG. 64 taken along lines 64A-64A;

FIG. 65 shows another embodiment of a rectangular or square crimp post;

FIG. 65A is a sectional view of the structure of FIG. 65 taken along lines 65A-65A;

DETAILED DESCRIPTION OF THE PREFERRED EMBODIMENTS

Figure 1:
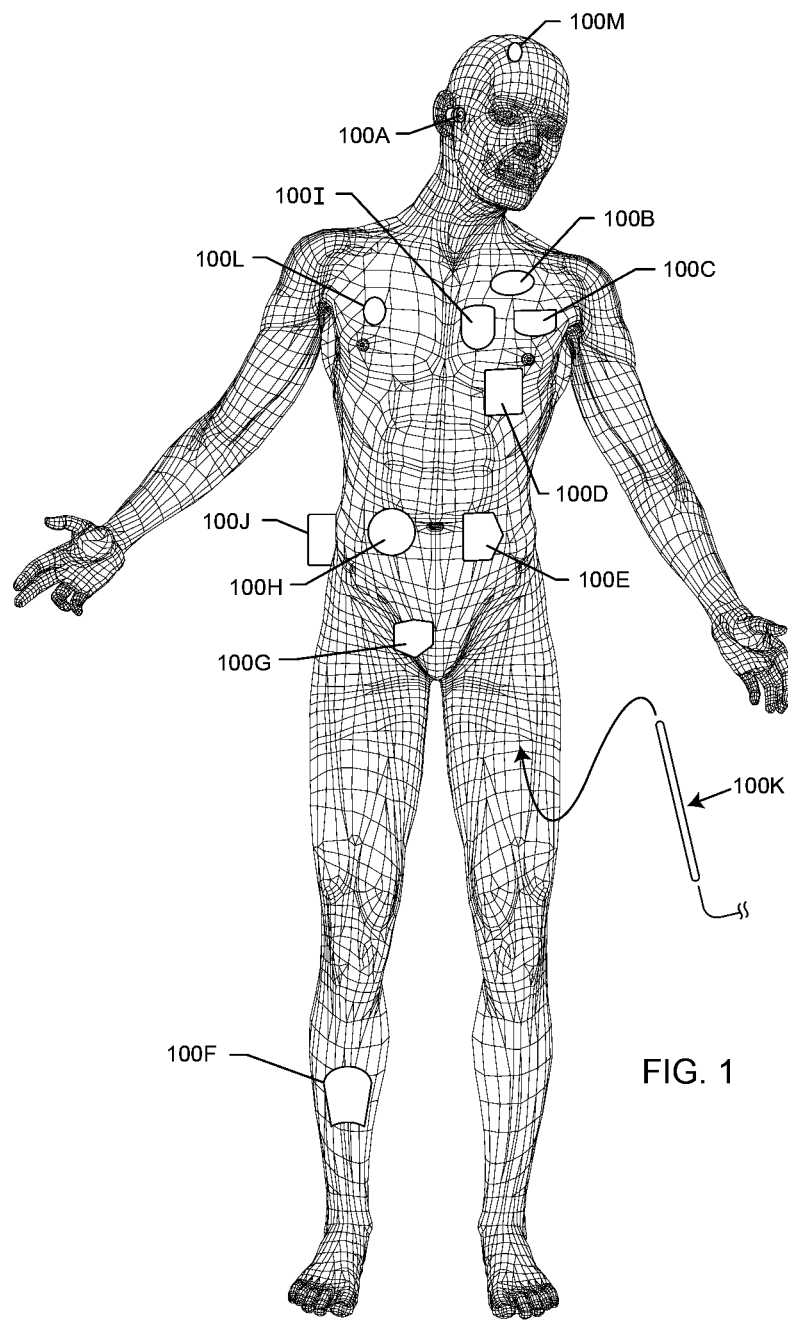
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. 100K illustrates the insertion of an external probe or catheter. These probes can be inserted into the femoral artery, for example, or in any other number of locations in the human body.

As used herein, the term "lead" refers to an implantable lead containing a lead body and one or more internal lead conductors. A "lead conductor" refers to the conductor that is inside of an implanted lead body. As used herein, the term "leadwire" refers to wiring that is either inside of the active implantable medical device (AIMD) housing or inside of the AIMD header block assembly or both. As used herein, the term header block is the biocompatible material that attaches between the AIMD housing and the lead. The term header block connector assembly refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

It is understood that "vias" are defined as holes, apertures, conduits, or voids created in either insulators or capacitors. A via can also be filled with a conductive material or bore-coated with a conductive material such that the inside surface is metalized and conductively coated. A via in a capacitor will generally be referred to as a capacitor via. A via in an insulator will generally be referred to as an insulator via. Accordingly, the terms filled or bore-coated can also be applied to either capacitor vias or insulator vias.

Figure 2:
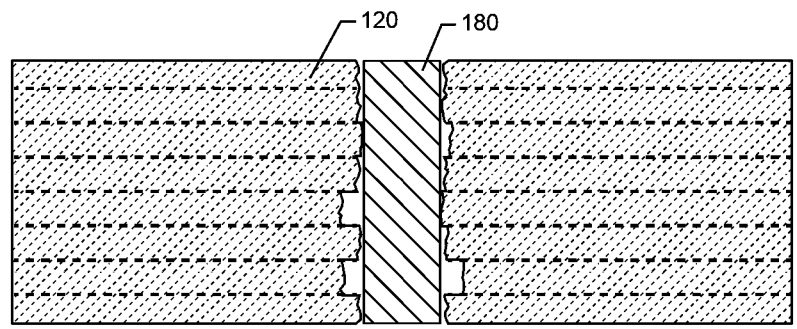
FIG. 2 is a sectional view of a hermetic insulator with a solid metallic filled via in a green state.
Figure 3:
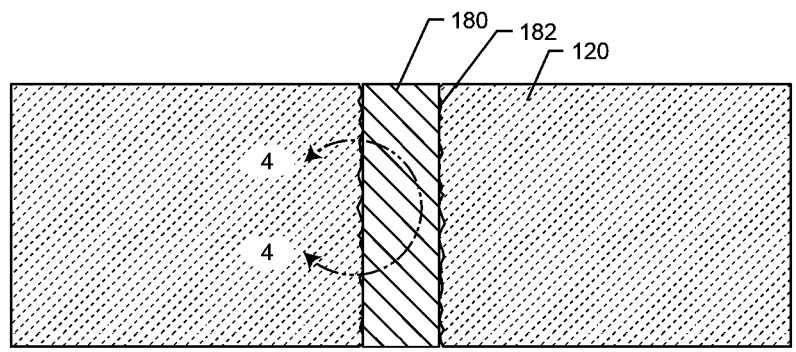
FIG. 3 is a sectional view of the structure of FIG. 2 now after sintering.
Figure 4:
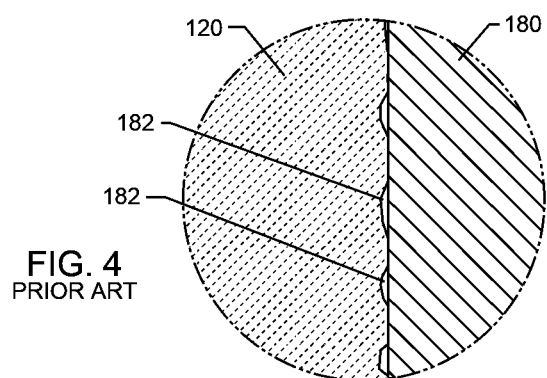
FIG. 4 is an enlarged view taken from FIG. 3 along lines 4-4 now showing gaps between the solid metallic leadwire and the insulator.

FIG. 2 illustrates a prior art cross-section of a different type of hermetic terminal subassembly substrate. The insulator 120 is a ceramic substrate formed by roll compaction. After compaction, the leadwire 180 is placed within the insulator via. In this case, the insulator via is filled with a solid platinum leadwire 180. FIG. 4 is an enlarged view taken from FIG. 3 showing gaps 182 that are created between the insulator 120 and the leadwire 180. These gaps reduce hermeticity and are very problematic.

One is referred to U.S. Pat. Nos. 7,480,988; 7,989,080; and 8,163,397. These three patents share a common priority chain and are directed to a method and apparatus for providing a hermetic electrical feedthrough. All three of these patents were assigned to Second Sight Medical Products, Inc. and will hereinafter be referred to as the "Second Sight" patents. FIG. 3 of the Second Sight patents is a flow process that starts with drilling blind holes in a green ceramic sheet. Then lengths of platinum leadwire 180 are cut and inserted into the sheet holes in step 39. The ceramic wire assembly is then fired at 1600° C. in step 44. Second Sight discloses that "during the firing and subsequent cooling, the ceramic expands shrinking the holes around the wires 38 to form a compression seal. The shrinkage is believed to occur, at least in part, as a consequence of polymer binder burnout. The fine aluminum oxide suspension permits uniform and continuous sealing around the surface of the wire. Additionally, at the maximum firing temperature, e.g., 1600° C., the solid platinum wires being squeezed by the ceramic exhibit sufficient plasticity to enable the platinum to flow and fill any crevices. This action produces a hermetic metal/ceramic interface." Further, Second Sight discusses that "After lapping, the feedthrough assembly comprised of the finished ceramic sheet and feedthrough wires, is subjected to a hermeticity test, e.g., frequently a helium leak test as represented by block 56 in FIG. 3." While Second Sight discusses forming a compression seal and platinum flow to fill any crevices, creation of mutually conformal interface or tortuous, intimate knitline between the alumina and the platinum wire is not taught.

In addition, latent hermetic failures in device feedthrough terminals have been known to occur due to susceptibility of the glass phased interface between these mating materials to erosion by body fluids. This outcome is particularly prevalent for interfaces comprising silicate glasses that are often a result of the additives to ceramic slurries forming the tapes and via fill materials that are used to build multilayer ceramic feedthrough structures. Dissolution of silicate glasses is composition dependent. In particular, erosion of silicate glasses in the body typically occurs when the silica content is lower than about 60%. Silica glasses, as suggested by the name, are based on a tetrahedral network of atoms comprising silicon and oxygen covalently bonded to each other. Heat treatment during the assembly process of the feedthrough structure provides the means by which other elements, such as alkali and/or alkaline ions, can be introduced into the silica atomic network. When the glass composition formed at the interface is more than 60% silica, the atomic network within the glass structure typically becomes resistant to reaction with body fluids due to the dense nature of the atomic network structure. However, when the glass composition formed at the interface is less than about 60%, the glass structure is more susceptible to atomic structural degradation.

Degradation is generally due to the disruption of the silica atomic network within the glass structure by other elements, such as alkali and/or alkaline ions, introduced during binder bake out and sintering. These other elements are typically introduced into the feedthrough structure from additives used within the green alumina tape or the via fill materials, such as the platinum paste, or both. For example, if the additives in either material make available alkali-metal atoms for exchange with silicon atoms within the silica atomic network, and if the result is an interface having a silica weight percent below about 60%, then rapid ion exchange of the alkali-metal cations with hydrogen ions from body fluid typically occurs. This results in the formation of functional hydroxyl, or —OH, groups that are highly reactive in the body, breaking down and weakening the atomic network structure of the glass phased interface thus increasing the likelihood of a breach in the hermeticity of the feedthrough terminal. Hence, hermetic structures created by mating alumina and platinum are not obvious and any inherency in the bond developed between these two materials does not necessarily result in a biocompatible final structure that can sustain hermeticity over the service life of an AIMD.

There are a number of patents that disclose hermetic terminals manufactured by a co-fire process and based on an alumina ceramic with platinum paste filled vias such as the following: U.S. Pat. No. 5,782,891 to Hassler et al.; U.S. Pat. No. 6,146,743 to Haq et al.; U.S. Pat. No. 6,414,835 to Wolf et al.; U.S. Pat. No. 8,000,804 to Wessendorf et al.; U.S. Pat. No. 8,043,454 to Jiang et al.; and US Published Applications 2007/0236861 to Burdon et al.; 2007/00609969 to Burdon at al.; 2011/0102967 to Munns et al.; and 2011/0248184 to Shah. None of the prior art concepts, however, including the prominent concepts noted above, teaches a structure that has a mutually conformal interface, also called a tortuous, intimate knitline, that results in sustainable hermeticity for an AIMD. Further, none of the prior art, including the prominent concepts noted above, teach a structure, or the manufacture of such a structure, having residual stress levels such that either matched hermetic structures or structures that have protectively compressive stresses from the ceramic part to the filled via at the bonding interface are created.

In more detail, U.S. Pat. No. 8,043,454 to Jiang et al. (hereafter referred to as Jiang) describes a method of making a hermetic via in a ceramic substrate that is composed of a noble metal powder in a glass-free paste that contains alumina and a mixture of niobium pentoxide. The addition of the niobium pentoxide to the pre-sintered paste prevents shrinkage of the paste during thermal processing and binds to both the ceramic and the noble metal particulates in the via, thus maintaining a hermetic seal around the via. Hence, hermeticity in this case is imparted by niobium pentoxide and not a mutually conformal interface or tortuous, intimate knitline for a single straight via. Jiang teaches avoiding CTE mismatches for feedthroughs and compression seals formed by metal tubing on ceramic insulators, however, Jiang does not teach structures wherein shrinkage of the ceramic is greater than shrinkage of the filled via material. Further Jiang does not teach a terminal or feedthrough having residual stress levels such that matched hermetic structures or structures that have protectively compressive stresses from the ceramic part to the filled via material at the bonding interface are created.

In more detail, U.S. Pat. No. 6,146,743 to Haq et al. (hereafter referred to as Haq) teaches hermetically sealed multilayer substrates with vias. One is directed to Haq FIG. 16 which shows the cross section of via fill after sintering. Haq discloses that in this structure the "ceramic powder component also improves the degree of adhesion between the ceramic forming the substrate itself and external via 66, thereby ensuring the formation of a hermetic seal in ceramic substrate 50. This hermetic seal inhibits or prevents internal metallization layers 64 from becoming oxidized when substrate 50 is air-fired during one method of the present invention." One is directed to Haq column 21, lines 32-43 where towards the end of that paragraph it states, "As the unfired green tape material emerges from the casting tape machine, it is coated with a castable dielectric composition that upon firing at high temperatures forms a glass." It is the external via that imparts hermeticity of the internal vias in this structure, and not a mutually conformal interface or tortuous, intimate knitline for a single straight via. Regarding shrinkage, Haq teaches matching shrinkages between ceramic and filled via material. Haq does not teach a structure wherein shrinkage of the ceramic is greater than shrinkage of the filled via material. Further Haq does not teach a terminal or feedthrough having residual stress levels such that matched hermetic structures or structures that have protectively compressive stresses from the ceramic part to the filled via material at the bonding interface are created.

In more detail, U.S. Pat. No. 8,000,804 to Wessendorf et al. (hereafter referred to as Wessendorf) illustrates an electrode array for a neurostimulator. The Wessendorf patent teaches "a plurality of electrodes arranged in a two-dimensional array and extending through the ceramic base between the first and second major surfaces; a ceramic lid having a plurality of electrical connections extending therethrough, with the ceramic lid being attachable to the ceramic base to form a hermetically-sealed interior region; and an electronic circuit (e.g. a demultiplexer circuit) located within the hermetically-sealed interior region." Hermeticity in this case is imparted by "a two-part ceramic package which can be hermetically sealed" and not by a mutually conformal interface or tortuous, intimate knitline for each single straight via. Wessendorf teaches matching CTEs for ceramic and via fill materials, however, Wessendorf does not teach structures wherein shrinkage of the ceramic is greater than shrinkage of the filled via material. Further Wessendorf does not teach a terminal or feedthrough having residual stress levels such that matched hermetic structures or structures that have protectively compressive stresses from the ceramic part to the filled via material at the bonding interface are created.

Figure 11:
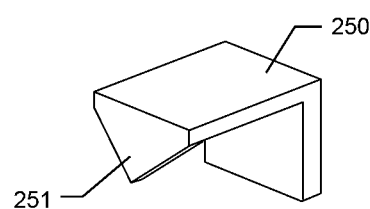
FIG. 11 is a perspective view of an exemplary wire bond pad.
Figure 12:
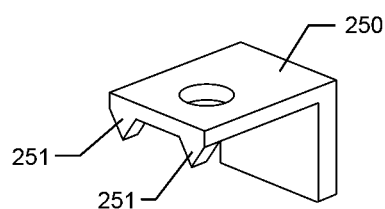
FIG. 12 is a perspective view of another exemplary wire bond pad.
Figure 13:
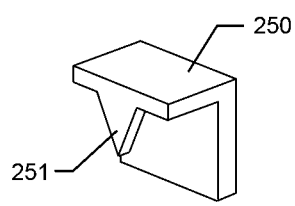
FIG. 13 is a perspective view of another exemplary wire bond pad.
Figure 14:
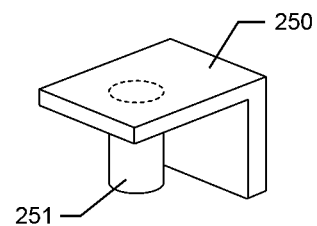
FIG. 14 is a perspective view of another exemplary wire bond pad.

Referring now to U.S. Pat. No. 8,043,454 of Jiang et al., and in sharp contrast to the present invention, Jiang adds between 1-10 percent by weight of niobium pentoxide. Another way to look at this is in the present invention, organic binders and solvents are used as opposed to inorganic additives. Additives to the platinum via fill 180 such as disclosed by Haq may result in unfavorable functionality. For example, the elongate channel-like structures that are actually a result of additives like ceramic powder can lower electrical conductivity if the conductivities of these phases are significantly different from the primary densified material formed. This is discussed in some of the prior art cited. It is very important for human implant applications that the resistivity of the filled via holes be as low as possible. The inventors have found that adding any ceramic powder to the platinum paste substantially increases the electrical resistivity of the post sintered via hole. This is a major reason why the inventors have been working over a number of years to develop a pure platinum sintered via hole. This is particularly important for AIMDs, such as implantable cardioverter defibrillators. An implantable cardioverter defibrillator not only senses electrical activity, but it must be able to deliver a very high voltage and high current shock in order to defibrillate the patient. This means that the entire system, including the lead conductors, the hermetic terminal subassembly via holes, and associated internal circuitry must have very low resistance and low impedance so that a high current can be effectively delivered. Furthermore, and as noted above, the creation of a glassy-phased structure bond (item 184 in FIG. 11A from parent application Ser. No. 14/182, 569) has the potential problem of latent hermetic leaks when exposed to body fluid. The present invention resolves this issue.

In the present invention, a post sintered, essentially high purity alumina substrate 188 with one or more via holes 186 that pass from an outside surface of the alumina substrate 188 to an inside surface of the alumina substrate 188 is provided wherein, the via holes 186 comprise a non-toxic and biocompatible post sintered, essentially pure platinum fill. There are several differences between the present invention and the prior art in addition to those specifically discussed in the brief overview of specific art cited. In the prior art, typically various additives are used to modify the alumina ceramic and/or the platinum paste. In the prior art, at times, it is not even a pure platinum paste that is used (see Wessendorf column 5, line 29), but rather one containing other refractory type materials, such as tungsten or the like. These additives are used to match the CTE during fabrication. In other words, these prior art systems go to a lot of effort to match the ceramic and metal parts of the system so that cracking or loss of hermeticity between the alumina substrate 188 and via 186 does not occur over time. Additionally, much of the prior art processes lay down a thin layer of ceramic tape, then use thick-film screen printing or other methods to deposit circuit traces and filler for the previously fabricated via holes 180. These fillers include tungsten inks and the like. Then, these individual layers are dried, stacked up and pressed (laminated) into a bar. There are often registration errors and stair-stepping is visible in the cross-sections of such vias 180.

In the present invention, via holes are not formed in individual tape layers before stack-up. Instead, the alumina ceramic slurry can be thick-cast into tape and then laid down in layers or it may be injected, molded, powder pressed or the like to form a single monolithic structure. In this state, the alumina ceramic is still in the green and very pliable due to the organic binders and solvents that have been temporarily added to the system. It is at this point that via holes 186 are drilled therethrough from the outer surface (body fluid side) to an inner surface (AIMD electronic side) of the alumina substrate 188. Because the holes are drilled after formation of the pre-sintered ceramic substrate 188, there is no requirement for registration with the consequential "stair-stepping" (due to misregistration) that is visible in cross sections of some prior art structures, for example those described in the Second Sight patents.

After via holes are formed, the pure platinum paste composition is injected under pressure or via vacuum into the via holes 186. The pressure or vacuum is carefully controlled in the present invention so that the platinum paste is driven intimately along the surface of the inside of the via such that the paste conforms to and creates a mirror image of the inner surface of the via in the alumina ceramic and, in so doing, interconnect with the already tortuous members prevalent in ceramic/particulate formation. A mutually conforming interface 191 is thereby formed between the platinum fill and the inside diameter of the via hole in the ceramic. (See FIG. 42) Drilling is a preferred method of forming the via hole, but these via holes may also be formed by punching, laser drilling, water cutting or any other equivalent process.

As used herein, the term "essentially high purity alumina" means alumina ceramic with the chemical formula $Al_2O_3$. "Essentially pure" means that the post-sintered ceramic is at least 96% alumina. In a preferred embodiment, the post-sintered ceramic is at least 99% high purity alumina. Prior to sintering, the alumina may be a paste, a slurry or green state, and can contain organic solvents and binders. Once these organic solvents and binders are baked out, the alumina is sintered becoming essentially high purity alumina. Similarly, prior to sintering, the platinum paste also contains binders and solvents. The drilled vias of the ceramic insulator are filled with the platinum paste. It is after the binders and solvents are baked out at elevated temperature and then sintered that they are substantially removed and an essentially pure platinum via hole is created.

Figure 5:
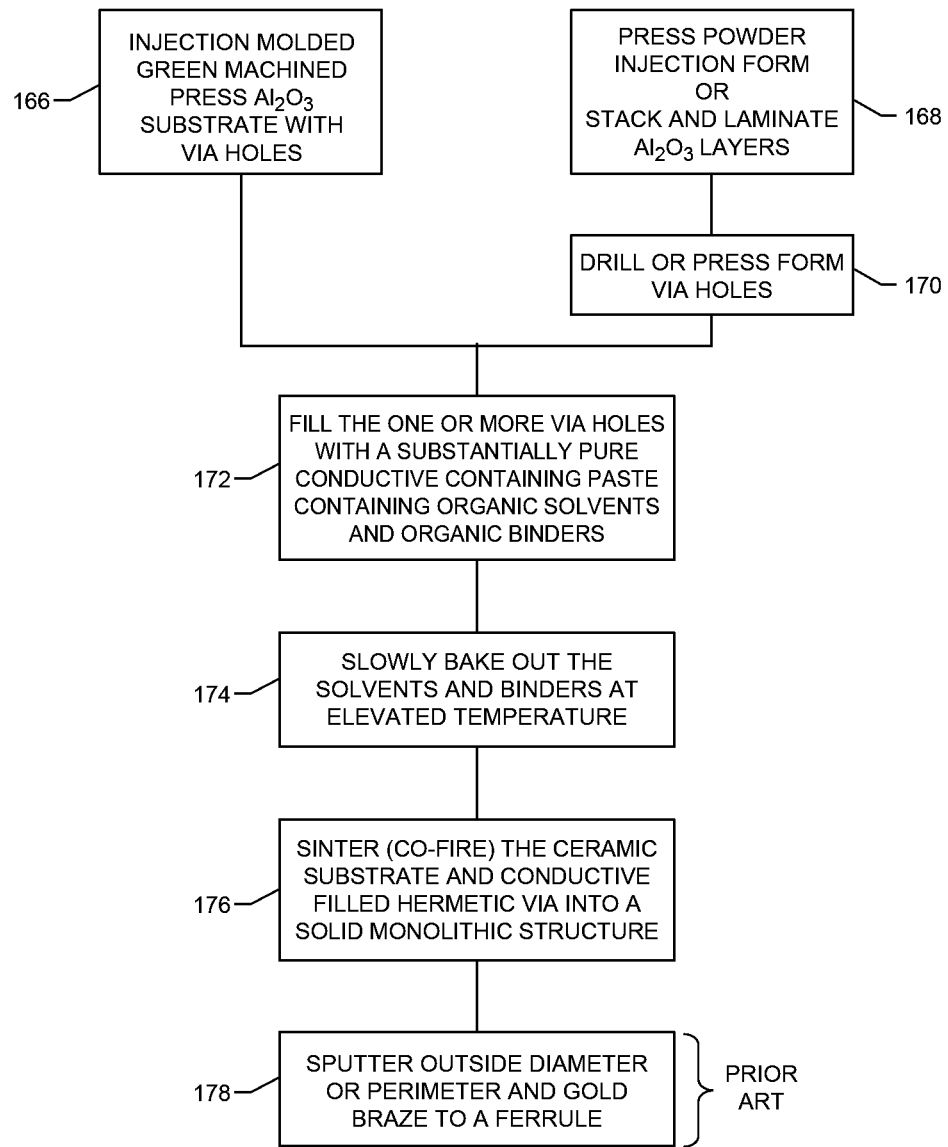
FIG. 5 is a flow chart illustrating the main steps of one embodiment of the process of the present invention.

One is referred to FIG. 5 which is a flow chart illustrating the main steps of the process of the present invention. First, an essentially high purity alumina substrate is formed. The essentially high purity alumina can be formed either through injection molding, green machining, powder pressing 166, by pressing powder into an injection die, or by tape casting and then stacking and laminating individual layers, under a pressure ranging from about 1,000 psi to about 5,000 psi at a temperature ranging from about 60° C. to about 85° C. for about 5 minutes to about 15 minutes into a bar 168. After formation of the bar in step 168, the via holes are formed preferably by drilling through the structure, however punching, pressing, laser or waterjet operations may also be used to form the holes 170. All of the via holes would be filled in step 172 with an essentially pure platinum paste containing organic solvents and organic binders. It should be noted that organic solvents and binders also make up a percentage of the green essentially high purity alumina substrate. A further clarification is required here. As used herein, "essentially pure" means essentially pure post-sintering once the bulk of the binders and solvents have been baked out in step 174 and/or sintered in step 176, both at elevated temperature. Once the binders and solvents have been driven out of the system and sintering 176 has occurred, the result is a solid monolithic high purity alumina substrate 188 with one or more pure platinum via holes 186 extending from an alumina substrate 188 outer surface to an inner surface. The outside diameter or the perimeter of the alumina substrate can now be prepared for attaching a ferrule 122. In the present invention, the ferrule 122 is attached using conventional prior art techniques. That is, the outside diameter or perimeter of the sintered alumina substrate 188 is metalized (sputtered). The metallization would typically be in two layers with a first layer being an adhesion layer 152 and the second layer being a wetting layer 150. Then the ferrule is attached to these metalized ceramic layers through a gold brazing process 178 wherein, pure gold is reflowed such that it wets the titanium ferrule and also wets to the metalized surfaces that were previously sputtered onto the alumina ceramic.

The present invention centers around three enabling areas: (1) via packing with a high solids loading in the paste, (2) compression by the ceramic of the metal paste during binder bake out and sintering, and (3) a controlled cool down rate in combination with interfacial bonding sufficient to tolerate coefficient of thermal expansion (CTE) mismatch.

Metal/ceramic compatibility is an important factor in manufacturing hermetic terminals. The difference in CTEs of the metal and ceramic is recognized as a major parameter in predicting compatibility. The thermal expansion of metal is generally considerably greater than those of ceramics. For example, at a bakeout temperature of 500° C., the CTE of alumina is $7.8 \times 10^{-6}$/K and of platinum is $9.6 \times 10^{-6}$/K. Historically, CTE differences within 0.5 to $1.0 \times 10^{-6}$/K between the mating metal and ceramic materials are adequate to sustain hermetic bonding between these materials. However, it is believed differences beyond these limits provided at the bake out temperature for the alumina/platinum pair may produce sufficient tensile stresses at the interface during cool down to cause spontaneous bonding failure. Hence, given the significant difference in CTEs, even at a relatively low temperature of 500° C., achieving a hermetic seal between the platinum metal and alumina ceramic would not be expected if the difference in CTE between the sintered alumina and the platinum metal exceeds 0.5 to $1.0 \times 10^{-6}$/K. Rather, the present invention achieves a hermetic feedthrough structure through the controlled fabrication process parameters of the platinum metal particle solids loading within the paste, controlled packing of the platinum paste within the via, and the controlled shrinkage of the alumina substrate and platinum via paste through a prescribed co-fire heating profile.

In addition, a highly irregular surface at the material interface between the alumina substrate and the platinum metal particles within the via provides a mechanical contribution to adherence and robustness of the hermetic seal. A surface roughness produced by drill bits, sandblasting, grit-blasting or chemical etching of the metal substrate can increase the surface area and, in so doing, provide for a stronger mechanical attachment along the mutually conformal interface. Applying this concept to the alumina/platinum interface therein provides for another novel aspect of the present invention. Examples of sandblasting and gritblasting media include sand, sodium bicarbonate, walnut shells, alumina particles or other equivalent media.

In the present invention, to achieve sustainable hermeticity, the following is required. Because the CTE of platinum is sufficiently higher than the CTE of alumina, it is not theoretically possible for alumina to provide compressive forces on a platinum body in a via. Hence, to overcome the CTE differences between these two materials, the platinum body in the via must be formed using a paste, a slurry or the like, having a minimum of 80% solids loading. In one embodiment, the solids loading of the platinum particles within the paste is 90%. In another embodiment, the solids loading of the platinum particles within the paste is 95%. In addition, the via must be packed with the platinum paste to occupy at least 90% of the available space within each via opening. In an embodiment, the platinum paste is packed within the via opening to occupy 95% of the space. In another embodiment, the platinum paste is packed to occupy 99% of the via opening. The shrinkage of the alumina must be no greater than 20% of that of the platinum fill in the via. In an embodiment, shrinkage is 14%. In another embodiment, shrinkage is 16%.

Furthermore, the assembly is exposed to a controlled co-firing heating profile in ambient air that comprises a binder bakeout portion, a sintering portion and a cool down portion. A preferred binder bakeout is at a temperature of between 550° C. to 650° C. A more preferred binder bakeout is at a temperature of between 500° C. to 600° C. The sintering profile portion is preferably performed at a temperature ranging from 1,400° C. to 1,900° C. for up to 6 hours. A preferred sintering profile has a temperature between 1,500° C. to 1,800° C. A more preferred sintering temperature is between 1,600° C. to 1,700° C. The cool down portion occurs either by turning off the heating chamber and allowing the chamber to equalize to room temperature or, preferably by setting the cool down portion at a rate of up to 5° C./min from the hold temperature cooled down to about 1,000° C. At 1,000° C., the chamber is allowed to naturally equalize to room temperature. A more preferred cool down is at a rate of 1° C./min from the hold temperature to about 1,000° C. and then allowing the heating chamber to naturally equalize to room temperature. In so doing, the desired outcome of achieving a robust hermetic seal is achieved between the mating materials of the alumina and platinum. It is noted that these materials have a CTE mismatch beyond the limits heretofore recognized as adequate for sustained bonding.

During processing of the platinum fill densities and additionally during the densification phase, compression is imparted by the alumina around the platinum within the via due to the shrinkage of the alumina being greater than that of the platinum. Furthermore, the platinum is sufficiently malleable at this phase to favorably deform by the compressive forces being applied by the alumina. The combination of the platinum solids loading, the platinum packing in the via and the shrinkage of the alumina being greater than the platinum fill results in the platinum taking the shape of the mating alumina surface. The amount of platinum solids loading, its packing percentage within the via and the malleability of the platinum material all contribute to formation of a hermetic seal between the platinum and alumina. In addition, the compressive forces that result from the greater shrinkage of the alumina substrate than that of the platinum within the via limit expansion of the platinum and force the platinum to deform such that it forms a hermetic seal. Thus an interface between the alumina and platinum materials that conforms to the respective interface surfaces and results in a nearly exact mirror image of the interfacing surfaces is formed, thereby creating a hermetic bond therebetween. This mutually conformal interface is critical, particularly as researchers studying bonding between alumina and platinum believe that any strength in the bonding between the alumina and platinum is physical.

As noted earlier, strong bonding between the alumina and the platinum is the most important factor in achieving sustainable hermeticity in feedthrough terminals for AIMDs. The inventors have learned that the co-fire parameters used to form the hermetic terminals of the present invention provide unanticipated, but novel benefit of leveraging the catalytic nature of platinum, that is, platinum's affinity for certain elements, which enables either direct bonding or formation of an interfacial layer between the two materials. Analysis of the interface between the alumina and the platinum of this invention disclosed not only the creation of an intimate knitline, but, in the case of the interfacial layer, a hermetic structure that exhibits an amorphous layer at the knitline comprising the elements platinum, aluminum, carbon and oxygen that appears to impart resistance to erosion by body fluids. Both these bonding mechanisms, direct bonding and an amorphous interfacial layer, offer additional tolerance to the CTE mismatch between these two materials.

Figure 6:
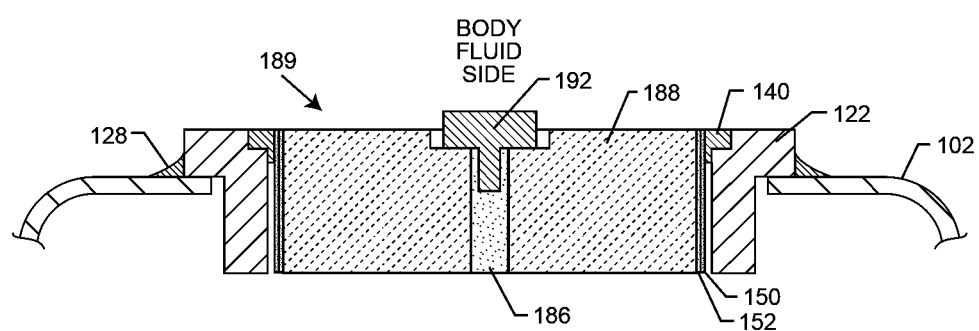
FIG. 6 is a sectional view of a feedthrough assembly now showing a wire bond cap co-fired into the platinum filled via.

FIG. 6 now shows a novel wire bond cap 192 has been placed on top of the via hole 186. In a preferred embodiment, this wire bond cap 192 could be of similar compatible metal, like pure platinum, such that it could be co-fired, to electrically and mechanically connect to the via hole fill material 186. This wire bond cap 192 can be placed on the top side as shown, or the bottom side, not shown, or both sides depending on the application and how wires would be routed to an implanted lead, an AIMD connector-header block, or the like. Referring once again to FIG. 6, the novel cap 192 can be set into a counter-bore hole as shown or it can be set flush or proud on the top surface of the alumina 188, or any variation thereof. Referring once again to FIG. 6, an implantable lead conductor could be connected to a wire bond cap 192 located on the body fluid side. In general, the implantable lead conductor or header block leadwire 118 would have a distal electrode in contact with biological cells.

It has been demonstrated that in a normal patient environment, a patient can be exposed to EMI. This EMI can take many forms, such as that from cellular telephones, airport radars, microwave ovens, and the like. A new international standard ISO 14117 has evolved, which includes tests standards to which cardiac pacemakers and implantable defibrillators must be exposed in order to be qualified by the FDA. There are similar specifications for cochlear implants and neurostimulators. Accordingly, it is important to provide EMI filtering at the point of lead conductor ingress into the interior of the AIMD. It is best to decouple high frequency interference before it gets inside of the AIMD housing 102.

Once inside an AIMD housing 102 the EMI can undesirably cross-couple or re-radiate to sensitive circuits where it can disrupt the proper functioning of the AIMD. In extreme cases, pacemaker inhibition has been documented which is immediately life-threatening for a pacemaker dependent patient. Accordingly, there is a need in the present invention, to provide for EMI filtering at the point of implanted lead ingress into the implanted medical device housing 102.

FIG. 7 shows an L-shaped wire bond cap 212. In this case, there is a hole in the wire bond cap through which a pin 242 is either laser welded, brazed or the like 238 to the L-shaped wire bond cap 212. This pin ideally would be of platinum or similar compatible metal. This assembly is co-fired along with the pure platinum via fill 186 so that a solid mechanical and electrical connection is made between the pin 240 and the platinum via material 186. There is also a difference in the way that the interior leadwires 118' are attached to the feedthrough capacitor 124. This is a special feedthrough capacitor that is rectangular in shape. The rectangular shape is better understood by looking at the cross-sectional views shown in FIGS. 8 and 9. FIG. 8 is taken generally along section 8-8 of FIG. 7. FIG. 9 is generally taken from section 9-9 of FIG. 7. The view in FIG. 7, therefore, is the end view of a rectangular structure. The active electrodes 134 are brought out to the sides of the capacitor, which is better illustrated in FIG. 8. This allows wire bond pads 246 to be attached to the capacitor. Attachment is done by thermal-setting conductive adhesives, gold braze, high temperature sold ers, or the like 248. The capacitor ground plate set 136 is terminated at its ends. This is important so that the ground plates 136 do not short to the active electrode plates 134. This makes subsequent attachment of interior leadwires 118' very easy. Internal leadwires 118' can be attached to the wire bond pads 246 by thermal sonic bonding, resistance bonding, resistance welding, soldering, thermal-setting conductive adhesives, brazes, or the like, 244.

Figure 10:
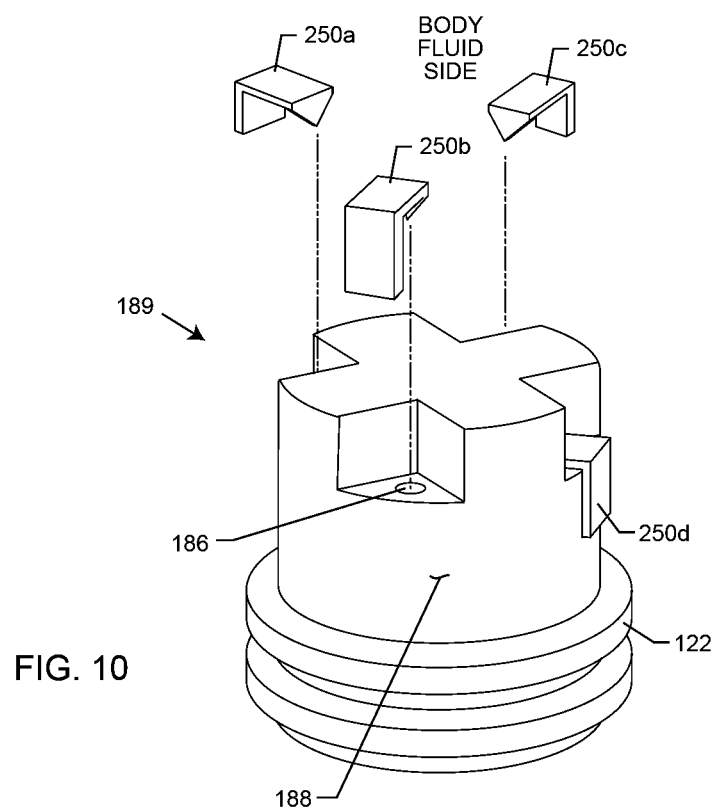
FIG. 10 is a perspective view of an exemplary embodiment of a round quad polar hermetic terminal assembly.

FIG. 10 illustrates a round quad polar co-fired high purity alumina ($Al_2O_3$) hermetic terminal subassembly with one or more pure platinum filled vias 186 of the present invention. Shown are novel L-shaped wire bond pads 250a through 250d, which can be co-fired with the pure platinum via hole fill 186. Since these wire bond pads 250 are on the body fluid side, it is important that they be non-toxic and biocompatible. Ideally, they would be of platinum or similar metal that was readily co-fired and matched to the CTE of the solid platinum via fill 186.

FIGS. 11 through 14 illustrate alternative shapes for the wire bond pads 250a through 250d previously illustrated in FIG. 10. Each wire bond pad has one or more respective downwardly extending extrusions 251 in order to penetrate the via hole platinum paste 186 so that when co-firing, a solid mechanical and electrical connection is made.

Figure 15:
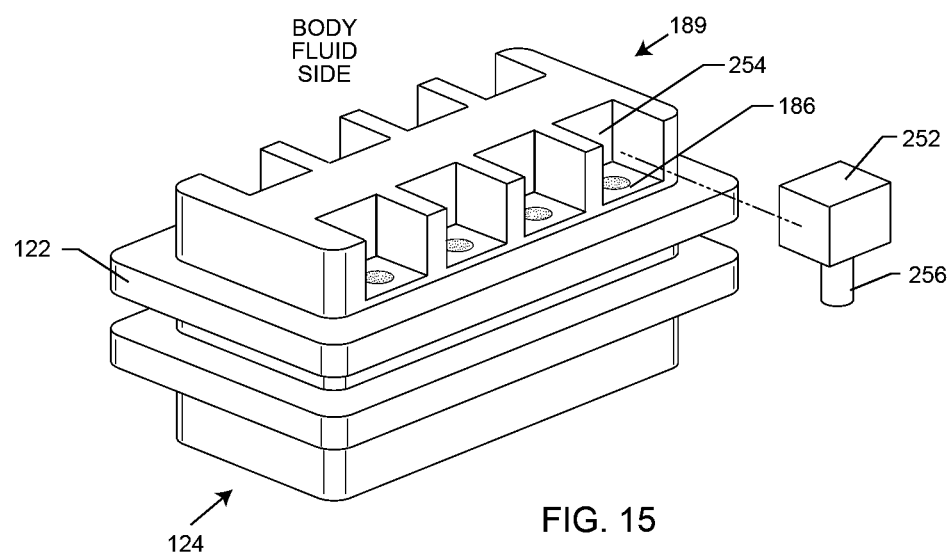
FIG. 15 is a perspective view of another exemplary embodiment of a rectangular hermetic terminal subassembly showing castellations.

FIG. 15 shows castellations 254 that have been made (into a square shape) and the corresponding wire bond pad 252 has also been made square. This structure would be much more robust during compressing welding operations during attachment of leadwires 118 where substantial force is pressed against the wire bond pad. Referring once again to FIG. 15, one can see that the wire bond pads 252 have a co-machined or co-formed post 256. This post would slip down into the via hole paste 186 and be co-fired. An ideal material for CTE match would, therefore, be a platinum post, however, gold, titanium, tantalum, palladium can all be used.

Figure 16:
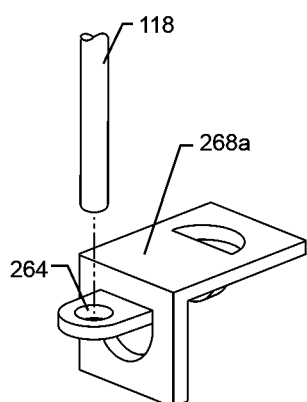
FIG. 16 is a perspective view of an embodiment of a wire bond pad.
Figure 17:
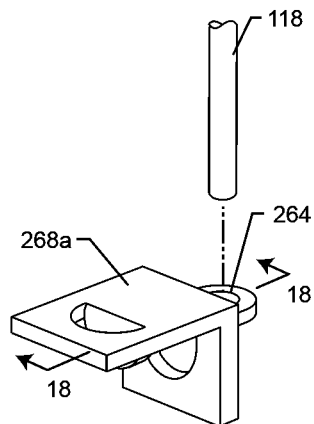
FIG. 17 is another perspective view of the embodiment of wire bond pad in FIG. 16.

FIGS. 16 through 23 show alternative embodiments of the header block connector assemblies such as those previously illustrated. FIGS. 16 and 17 illustrate stampings, which are ideally of platinum or some other similar biocompatible material. They have a hole 264 for convenient reception of leadwire 118 which may then be permanently attached by laser welding.

Figure 18:
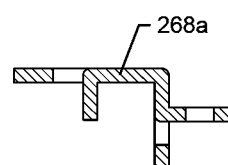
FIG. 18 is a sectional view of the structure of FIG. 17 taken along lines 18-18.

FIG. 18 is a sectional view 18-18 taken from FIG. 17 showing the stamping and cross-section.

Figure 19:
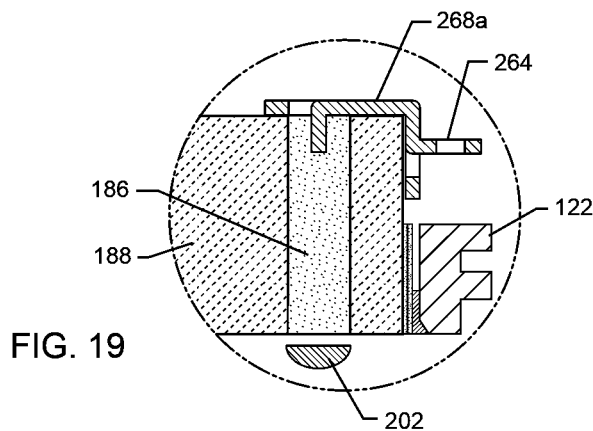
FIG. 19 is an enlarged sectional view of the wire bond pad of FIGS. 16-18 co-fired into the platinum filled via.

FIG. 19 is a sectional view showing the stamping of FIGS. 16, 17 and 18 co-fired into the novel platinum filled via 186 of the present invention.

FIGS. 20 and 21 illustrate another embodiment of stamping 268*b* now with fingers 265 that capture the leadwire 118.

FIG. 22 is an alternative embodiment for the header block connector assembly 268*c*, which in this case, has a leadwire 278. The leadwire may be attached to the bracket 268*c* by laser welding or the entire assembly could be co-machined or even formed by metal injection processes. In this case, the leadwire is a platinum or suitable biocompatible material that has a CTE that will match that of the platinum filled via 186. In this case, the leadwire 278 is co-fired with the platinum filled via material 186 to form a solid electrical and mechanical joint.

FIG. 23 is similar to FIG. 22 except that the header block connector assembly 268*d* has a convenient hole 264 for insertion of the leadwire 118 (not shown) where it can be laser welded.

Figure 24:
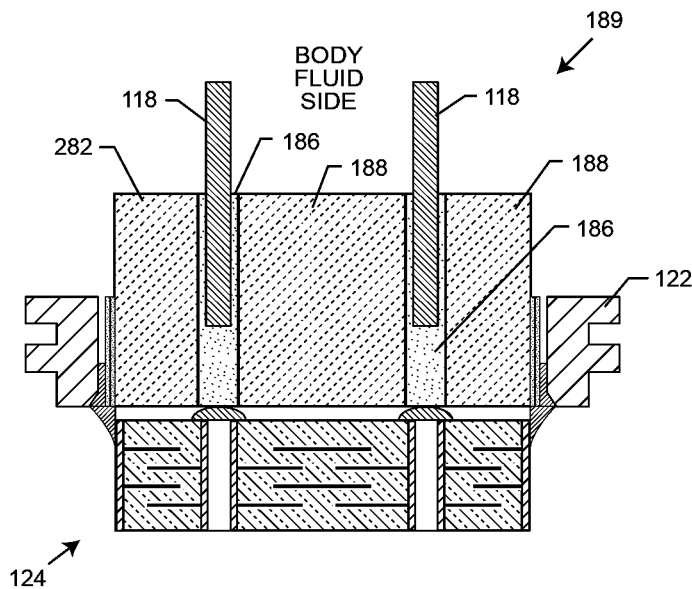
FIG. 24 is a sectional view of another exemplary embodiment of a hermetic terminal subassembly now showing a solid wire co-fired into the platinum filled via.

FIG. 24 illustrates a co-fired high purity alumina ($Al_2O_3$) hermetic terminal subassembly 189 with one or more pure platinum filled vias 186 of the present invention, wherein leadwires 118 have been co-fired into the platinum filled vias 186. In other words, the leadwire 118 is co-fired with the alumina 188 and with the platinum filled via 186, all in one single operation. Leadwires 118 would be routed and connected to implantable lead conductors or header block connector assemblies, as is well known in the prior art. As an alternative to a platinum leadwire 118, the leadwire 118 may comprise iridium, rhodium, niobium if a reducing atmosphere is used or palladium in air if the sintering temperature is low enough.

Figure 25:
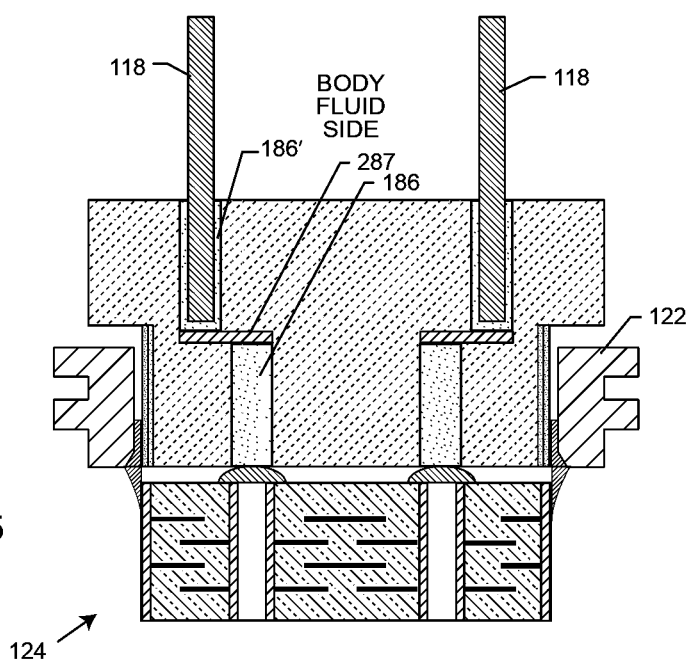
FIG. 25 is a sectional view similar to FIG. 24 now showing a staggered via hole with a solid wire co-fired into the platinum filled via.

FIG. 25 shows that there are staggered vias 186 and 186' that are filled with pure platinum and connected by a circuit trace 287 between the stagger. In this case, platinum leadwires 118 have been co-fired into the upper vias 186'. As previously stated, these leadwires 118 could be routed to implanted leads, to implanted distal electrodes or header block connector assemblies of AIMDs. The staggered via is a way of increasing the reliability and hermeticity of the overall structure.

Figure 26:
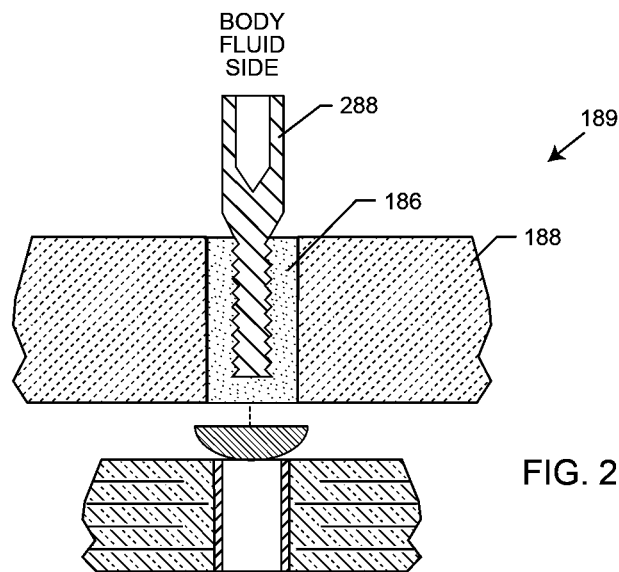
FIG. 26 is a sectional view of an exemplary embodiment of a crimp post co-fired into the platinum filled via.

FIG. 26 illustrates the co-firing of a novel crimp post 288 into the platinum filled via 186. Ideally, the crimp post would be of platinum or similar biocompatible material, which would have a CTE which closely matches that of platinum. A leadwire 118 (not shown) would be inserted into the crimp post and then a mechanical crimping tool would be used to form a mechanical and electrical connection between the walls of the crimp post and the lead 118. An optional or supplementary laser weld could also be performed at the point where the leadwire 118 is inserted into the top of the crimp post 288.

Figure 27:
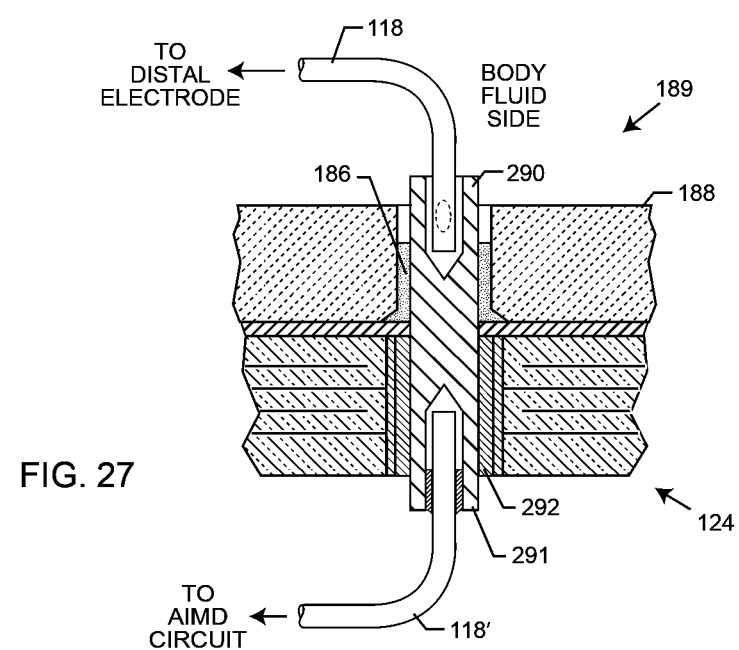
FIG. 27 is a sectional view of an exemplary embodiment of a double crimp post co-fired into the platinum filled via.

FIG. 27 is similar to FIG. 26, but illustrates a double crimp post. On the body fluid side, lead 118 is crimped into the crimp post 290 as shown. On the device inside, a wire 118' can be inserted and crimped into the opposite side 291 of the crimp post 290 to make connection to internal AIMD circuits. As described before, leadwire 118' could be an inexpensive copper insulated leadwire or, as in this case, a bare leadwire.

Figure 28:
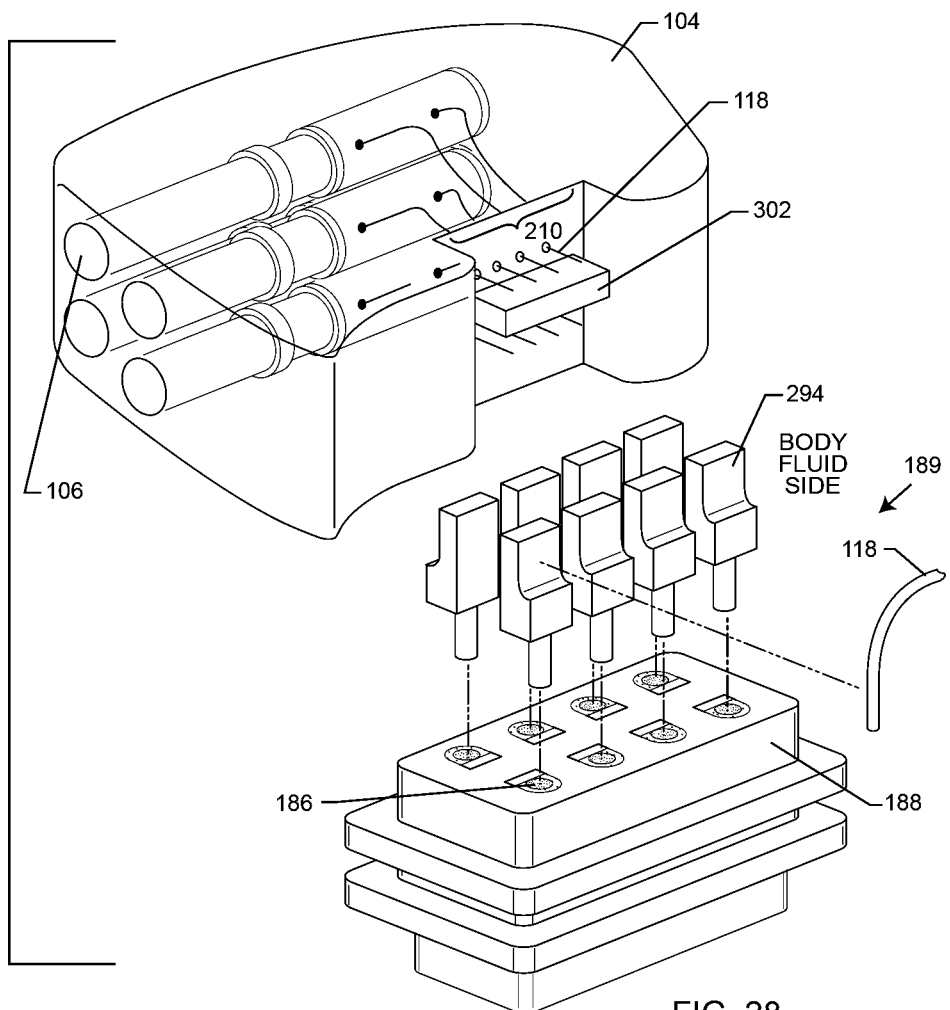
FIG. 28 is a perspective view of an exemplary embodiment of a novel method of header block connector assembly attachment showing a support structure behind the wire bond pads.

FIG. 28 illustrates a novel method of header block connector assembly attachment. The header block connector assembly 104 has been completely prefabricated in accordance with the present invention and has leadwires 118 extending down into a novel window 210 of the present invention. Co-molded or co-formed with the header block connector assembly 104 is a support structure 302. The header block connector assembly 104 is shown tilted 90°. There is a co-fired high purity alumina ($Al_2O_3$) hermetic terminal subassembly 189 with one or more pure platinum filled vias 186 of the present invention with novel wire bond post 294. These wire bond posts 294 each have a leadwire protrusion which are inserted into the via holes and are co-fired with the pure platinum 186. The support structure 302 is designed to slip between the two rows of bonding posts 294 and provide back support for them. That is, when one pushes against leadwire 118 very firmly with a resistance welder, this will prevent a platinum or equivalent post (which are very ductile) from deforming.

Figure 29:
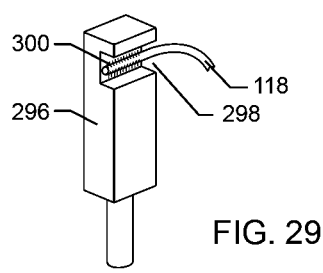
FIG. 29 is a perspective view of a wire bond pad similar to FIG. 28 now with a novel slot.

FIG. 29 illustrates a different type of post 296 which could be used in FIG. 28. Post 296 has a novel slot 298 which can receive leadwire 118 where a laser weld 300 or the like can be performed. The slot can also be formed and/or rotated 90 degrees such that it is aligned with the downward projecting leadwires 118.

Figure 30:
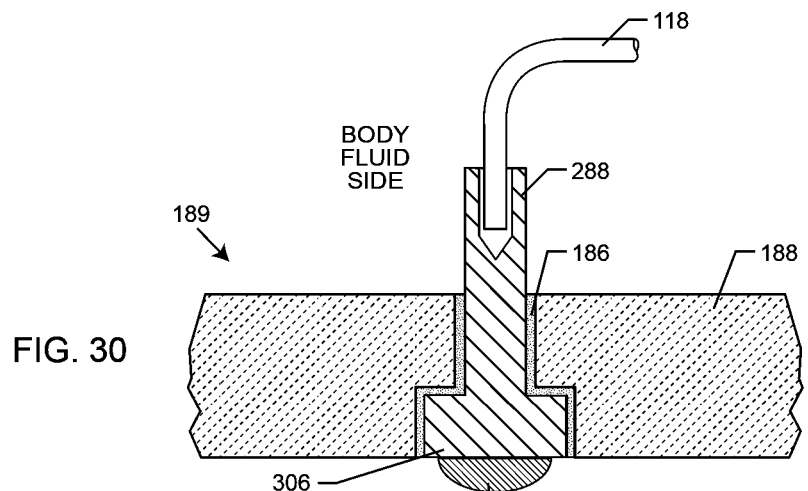
FIG. 30 is a sectional view with a novel crimp post co-fired into the platinum filled via.

FIG. 30 illustrates a co-fired high purity alumina ($Al_2O_3$) hermetic terminal subassembly 189 with one or more pure platinum filled vias 186 of the present invention with a novel crimp post 288 similar to that previously illustrated. In this case, the crimp post 288 is designed to receive an external leadwire 118 on the body fluid side. On the opposite side is the nail head structure 306, which could be radiused (not shown). In this case, the crimp post assembly 288 is ideally of platinum or similar material and is co-fired into the platinum filled via 186 in accordance with the present invention. A feedthrough capacitor 124 is attached using a solder BGA structure 202. It will be obvious to those skilled in the art that any of the BGA attachments as illustrated herein could also be solder dots, solder bumps or dots of thermal-setting conductive adhesives or epoxies, or the like. In a preferred embodiment, material 202 could be of thermal-setting conductive polyimide.

Figure 31:
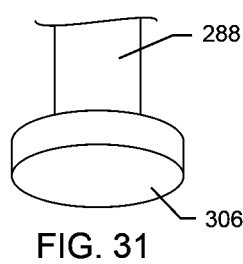
FIG. 31 is a perspective view of another exemplary embodiment of a novel crimp post similar to FIG. 30.
Figure 32:
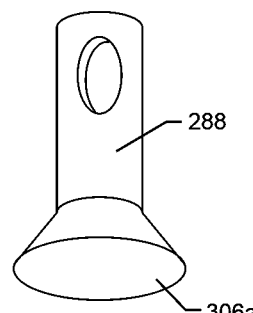
FIG. 32 is a perspective view of another exemplary embodiment of a novel crimp post similar to FIG. 30.
Figure 33:
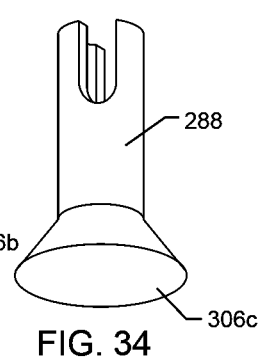
FIG. 33 is a perspective view of another exemplary embodiment of a novel crimp post similar to FIG. 30.
Figure 34:
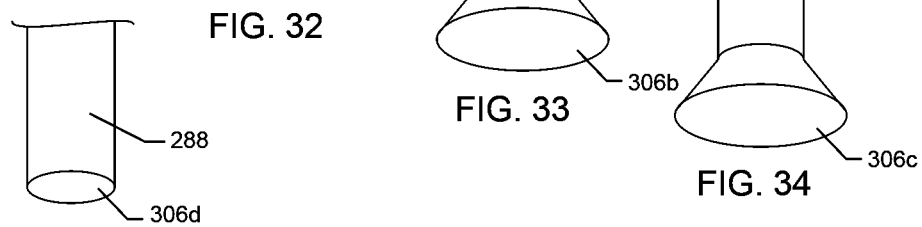
FIG. 34 is a perspective view of another exemplary embodiment of a novel crimp post similar to FIG. 30.
Figure 35:
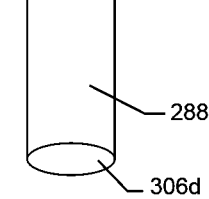
FIG. 35 is a perspective view of another exemplary embodiment of a novel crimp post similar to FIG. 30.

FIGS. 31 through 35 show alternative embodiments of the crimp posts 288. FIG. 31 illustrates the end view of the nail head 306 as previously illustrated in FIG. 30. FIGS. 32 through 35 illustrate alternative embodiments of the nail head structure 288 having respective nail head ends 306*a* through 306*d*.

FIG. 36 is an perspective view of a hermetic seal subassembly 101 shown laser welded 128 into an opening in the housing 102 of an active implantable medical device, such as a cardiac pacemaker. The ferrule 122 is generally of titanium and in the art, is commonly laser welded 128 as shown to the device housing 102. There is also a hermetic seal sub-assembly 187. The hermetic seal sub-assembly 187 is co-fired along with conductive fill material 186 and a conductive insert 402 into insulator 188. The conductive insert 402 along with the conductive fill material 186 is all co-fired along with the formation of the alumina ceramic insulator 188. In a preferred embodiment, the conductive fill material 186 would be of substantially pure platinum material and the conductive insert 402 would be of pure platinum or a platinum alloy. Once the insulator sub-assembly 187 has been co-fired, its edges can then be metallized by sputtering 150, 152 such that the entire perimeter insulator substrate can be gold-brazed 140 into the inside racetrack-shaped opening of the conductive ferrule 122.

FIG. 37 shows the device side of the hermetic terminal sub-assembly shown of FIG. 36. FIG. 37 is very similar to FIG. 36 except that the unit has been flipped over so one can see the device side on top. Referring once again to FIG. 37 on the device side, there would be electrical connections (not shown) to the ends of the conductive insert 402 for attachment to appropriate location to AIMD electronic circuits. Referring to FIG. 36, on the body fluid side, there would also be conductive attachments that would connect between the conductive insert 402 and/or the conductive fill 186 to various connector locations within an AIMD header block (not shown). Some AIMDs do not have a header block and instead have a direct connection from an implanted lead to the hermetic seal conductor. In this case, an implanted lead (not shown) with five conductors, would be connected to the five terminal pad locations 402.

Figure 38:
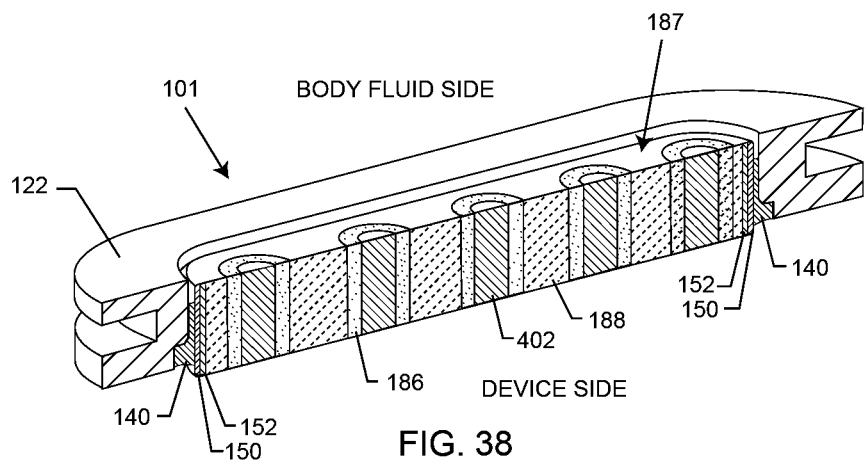
FIG. 38 is a sectional view taken generally from section 38-38 of FIG. 36.

FIG. 38 is taken generally from section 38-38 from FIG. 36 and shows the hermetic seal sub-assembly 101 in cross-sectional view. In FIG. 38, one can see the sputtered adhesion layer 152 which could consist of niobium or molybdenum and then followed by sputtering on of a wetting layer 150 of titanium or the like. Then gold braze material 140 can be flowed to the titanium ferrule 122 and to the wetting layer 150 thereby forming a robust, mechanical and hermetically sealed joint. As used herein, the term hermetic seal means that the hermetic seal sub-assembly, once it's installed in an AIMD housing, would have a helium leak rate of no greater than $1 \times 10^{-7}$ cubic centimeters per second. Referring again to FIG. 38, it is a feature of the present invention that the conductive fill material 186 is conductive from the body fluid side to the device side. The co-fired conductive insert, which at least partially fills the conductive via 186 is also conductive. In general, the conductive paste 186 has a certain resistivity after firing into the inside of the alumina insulator 188. In the present invention, the resistance from the body fluid side to the device side can be reduced significantly by adding a conductive insert 402 at least partially through the via hole from the device side to the body fluid side. In the case of FIG. 38, the conductive insert 402 penetrates all the way from the body fluid side to the device side and therefore would substantially improve the electrical conductivity between the body fluid side and the device side. In an embodiment, the resistance from the body fluid side to the device side would be no more than 2 to 10 milliohms.

Figure 39:
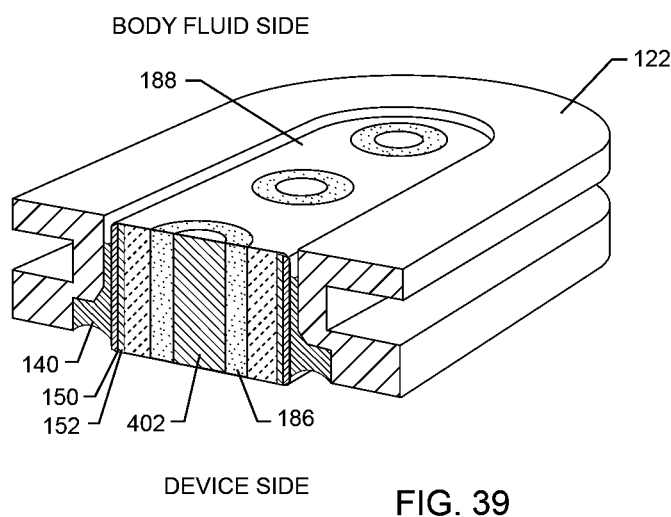
FIG. 39 is a sectional view taken generally from section 39-39 from FIG. 36.

FIG. 39 is taken from sectional view 39-39 from FIG. 36 giving one another view of the gold braze 140, the wetting layer 150 and the adhesion layer 152 that are all attached to the perimeter of the insulator 188.

Terminals for use in AIMDs comprising a structure co-fired into a conductive filled via for facilitating a wire attachment require compliance with the same hermeticity, durability, reliability and longevity criteria as expected of traditional hermetic terminal options. Achieving this result, however, offers significant challenge. The chemical, electrical, mechanical, thermal and manufacturing properties of the constituents comprising the material system collectively contribute to a sustainable AIMD terminal hermeticity. Hence, material selection, terminal design, assembly and co-firing methods are critical. For example, shrinkage and shrinkage rates may be matched to prevent development of damaging tensile stresses or selectively different to create compressive stresses that not only enable sustainable hermeticity but also support sustainable hermeticity from additional stresses imparted during wire attachment.

One embodiment of the present invention is directed to mating bound particulate conductive particles that are suspended within a mixture of solvents and binders, i.e., a paste, with a solid conductive structure. The solid conductive structure may be made from the same material as the particulate material, of a material with properties similar to the particulate material, or selectively chosen to be different from the particulate material to elicit a specific outcome, such as to create a hermetic compression terminal. The solid conductive structure may be pretreated to enhance bondability to the paste (e.g., to increase contact surface area of the solid conductive structure), formability for assembly (e.g., to reduce stresses imparted by working the material to form the solid conductive structure), wire attachment and the like.

Referring once again to FIG. 38, the conductive insert 402 that is embedded within the conductive filled via must result in an assembly that results in a conductive solid structure embedded within the conductive via, such that the packing of the conductive particulate in conjunction with the conductive solid within it does not alter the loading requirements to achieve the finished occupied space and resultant shrinkage for two reasons: achieving and sustaining hermeticity at the conductive paste/ceramic interface with controlled tensile stress levels or with ceramic shrinkage to result in a compressive terminal that sustains hermeticity and supports wire attachment loads.

Figure 40:
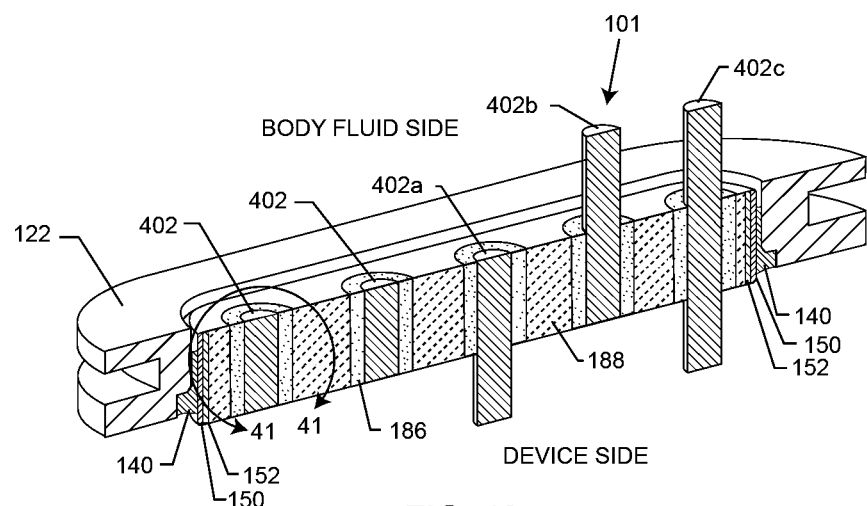
FIG. 40 is very similar to FIG. 38 except that in this case, the conductive inserts can be extended a considerable distance above or below the entire hermetic seal sub-assembly.

FIG. 40 is very similar to FIG. 36 except that in this case, the conductive inserts 402 can be extended a considerable distance above or below the entire hermetic seal sub-assembly. For example, conductive insert 402a is extended into the device side. This could be relatively short, as shown, or it could be several inches long to make suitable attachment to circuit attachment points. The same thing is true of the body fluid side as illustrated in conductive insert 402b, which extends towards the body fluid side. This could be made long enough to connect all the way to connector block attachment points (not shown). Insert 402c illustrates that the conductive insert could extend upwards into the body fluid side and also downward into the device side achieving both the aforementioned functions at the same time.

Figure 41:
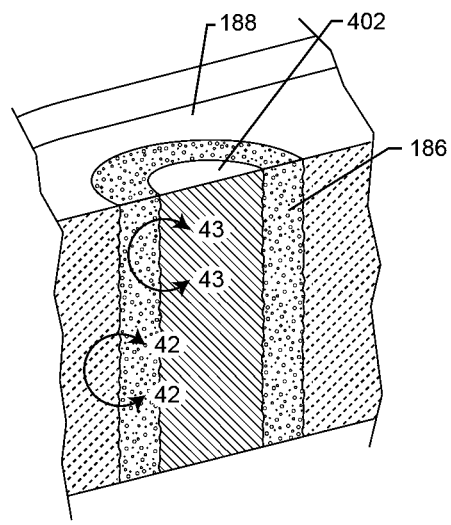
FIG. 41 is an enlarged view taken from the section at lines 41-41 from FIG. 40.

FIG. 41 is taken generally from sectional view 41-41 from FIG. 40. This shows a close-up view of the via filled with the conductive filled material 186 that is disposed and co-fired within the hermetic seal insulator 188. The conductive insert 402 is shown. Referring once again to FIG. 41, one can see that the surface of the conductive insert 402 has been roughened. For example, the solid conductive structure may be annealed, outgassed, plated, plasma etched, chemically etched, abraided, micro bead blasted, grit blasted, solvent cleaned, anodized, and the like prior to assembling and co-firing. The mating materials may be co-fired utilizing Low Temperature Co-Fired Ceramic (LTCC) or High Temperature Co-Fired Ceramic (HTCC) methodology, or some combination of both. Co-firing may also comprise additional steps, for example but not limited to, brazing, soldering or use of sacrificial volume materials.

Figure 42:
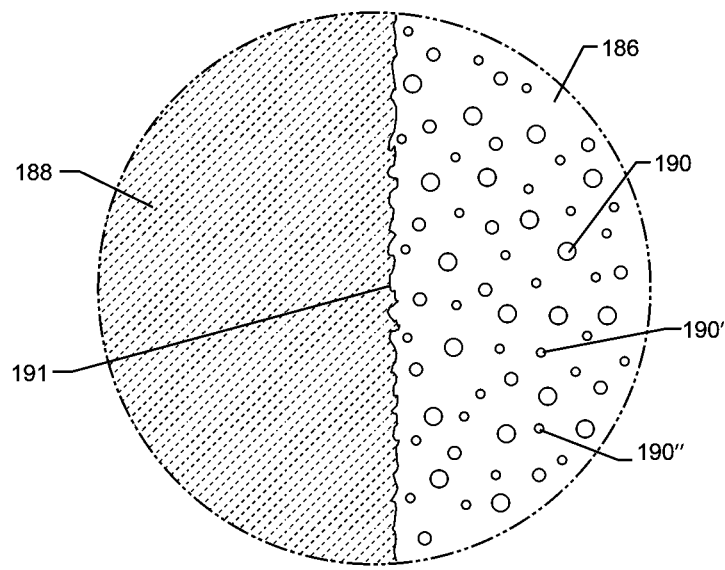
FIG. 42 is an enlarged view taken from the section at lines 42-42 from FIG. 41.

FIG. 42 is taken generally from partial section 42-42 from FIG. 41 and shows the mutually conforming interface between the conductive fill material 186 and the inside surface of the co-fired alumina ceramic insulator 188. As previously described in U.S. Pat. No. 8,653,384, the entire contents of which are incorporated herein by reference, one will see that this surface, as shown in FIG. 42, is torturous and mutually conforming, meaning that the peaks and valleys of this surface 191 are completely filled in by the closely co-bonded and fired conductive fill 186. This is very important to form both a physically strong and highly hermetic seal joint.

Figure 43:
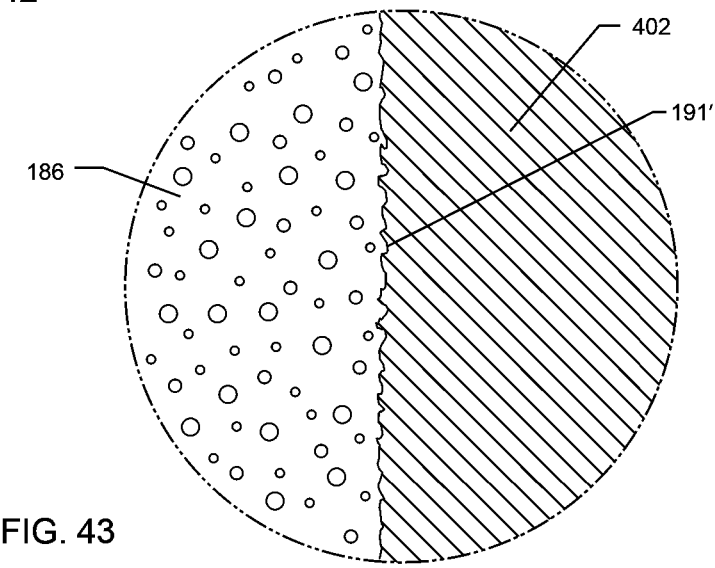
FIG. 43 is an enlarged view taken from the section at lines 43-43 from FIG. 41.

FIG. 43 is taken generally from partial section 43-43 from FIG. 41 and illustrates the highly desirable roughened surface 191' of the conductive insert 402. This roughened surface acts very similar to that previously described in FIG. 42 in that, this gives a place for the conductive fill material 186 to lock in and form a very mechanically strong and hermetic bond.

Referring once again to FIG. 42, one can see the interfacial knit line 191 that is formed between the co-fired alumina 188 and the conductive fill 186. In FIG. 42, one will notice that it is perfectly acceptable for the conductive fill to have some closed porosity holes 190 as shown. These can vary in size, as shown in 190' and 190". It is very important in the present invention and is previously described in U.S. Pat. No. 8,653,384 that these not be open cells such that a continuous hermetic leak path could be formed.

FIG. 43 shows a close-up of the knit line 191' that is formed between the conductive fill material 186 and the solid metal of conductive insert material 402. One can see that it is highly desirable that the surface 191' be rough and that the conductive fill material, upon co-firing, forms a tight bond thereby filling in all the peaks and valleys along that roughened surface.

Figure 44:
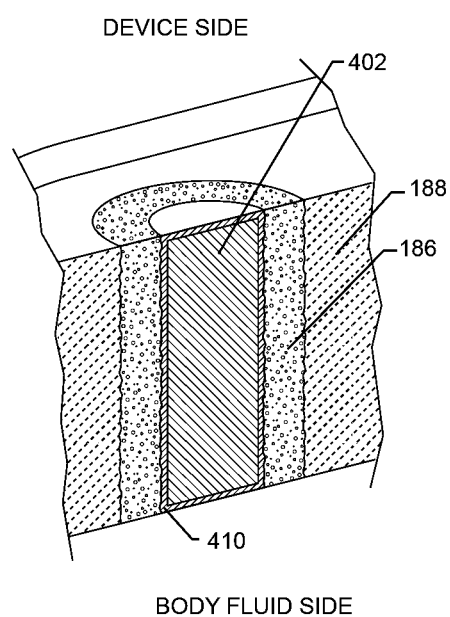
FIG. 44 is very similar to FIG. 41 except that the conductive insert is surrounded by a plating, a coating or a cladding material.

FIG. 44 is very similar to FIG. 41 except that the conductive insert 402 is surrounded by a plating, a coating or a cladding material 410. This type of structure is also known as drawn filled tubing. For example, the core or the inside of the conductive insert 402 could be of pure silver and the cladding 410 could be MP35N. The advantage of the silver would be extremely high conductivity and the advantage of the cladding would be to completely coat the silver, including particularly the body fluid side, such that the conductive insert was not only conductive, but also completely non-toxic and biocompatible. In one embodiment, it would only be necessary to have the biocompatible coating 410 on the body fluid side. Since body fluids cannot enter the hermetically sealed housing of the AIMD, it is not important for the device side to have a coating 410. In fact, it could be an advantage to enhance solderability or wire bond attachment to not have the cladding 410 on the device side as shown.

Figure 45:
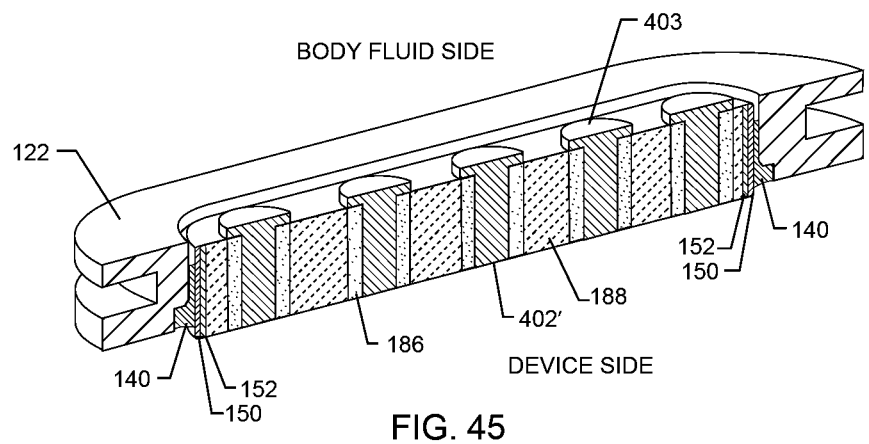
FIG. 45 is very similar to FIGS. 36-38 and is taken generally from section 45-45 from FIG. 36, except that now the conductive inserts have a nail head feature.

FIG. 45 is taken from section 45-45 of FIG. 36 and is very similar to FIG. 38 except that the conductive inserts 402' have a nail head feature 403. This provides a large surface area for which to attach a conductor, such as a lead conductor or a header block conductor by a laser weld or the like. Referring once again to FIG. 45, this nail head feature could be inverted and directed toward the device side. In this case, this would facilitate wire bonding, soldering or making connection to circuit boards on the inside of the device (not shown).

Figure 46:
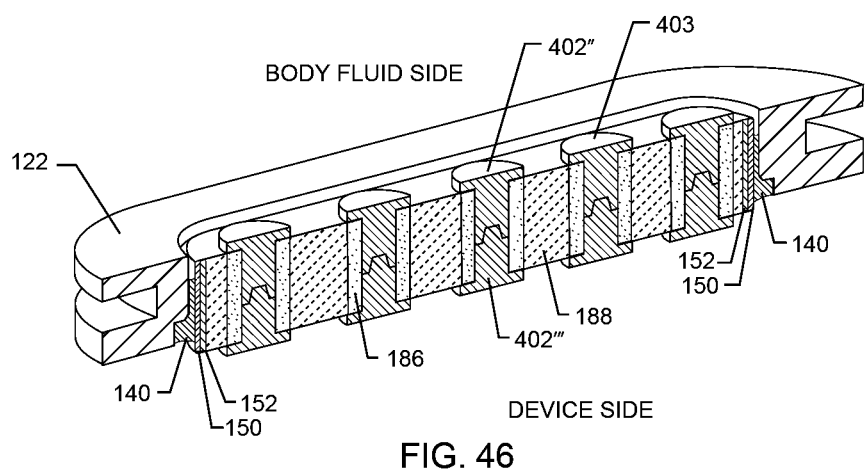
FIG. 46 is very similar to FIGS. 45 and 36-38 and is taken generally from section 46-46 from FIG. 36, except now shows a nail head feature on the top and bottom.

FIG. 46 is taken from section 46-46 of FIG. 36 and very similar to FIG. 45 which shows a nail head feature 403 on each of the inserts 402" and 402'''. Since the diameter of the via with the conductive fill 186 is smaller than the nail head, a two part construction is utilized. It is not necessary that a metallurgical bond be formed between the top 402" and the bottom 402''' of the conductive pads and conductive insert. The formula for resistivity is $R=\rho l/a$ wherein, $\rho$ is the resistivity, l is the length of the conductor and a is the cross-sectional area. So as long as the gap between the top conductive insert 402" and the bottom of the second conductive insert 402''' is not very great, then the resistivity from top to bottom will be desirably very low.

In the present invention, it is very important that the via consisting of fill material 186 and a solid insert 402 be of extremely low resistivity as measured from top to bottom. That is, from the body fluid side to the device side. There are a number of reasons for this. In a therapeutic pacing application, such as a cardiac pacemaker or a neurostimulator, pacing pulses pass from the device electronics through this filled via 186, 402 to an implanted lead and one or more of its associated electrodes. A voltage drop caused by excessive resistance in the via could not only degrade pacing pulses but it would also be wasteful of precious battery energy. Low resistivity is even more critical in high voltage pulse applications, such as for implantable cardioverter defibrillators. An ICD must deliver a very fast rise-time high voltage shock (above 700 volts) to properly cardiovert a fibrillating heart. If the rise-time of the magnitude of the pulse is degraded, it will not be nearly as effective. In summary, it is a primary feature of the present invention that a co-fired filled via hole be achieved, which is extremely low in resistance from the device side to the body fluid side. In an embodiment, this resistance would be less than 10 milliohms. In another embodiment, this resistance would be less than 2 milliohms.

Figure 47:
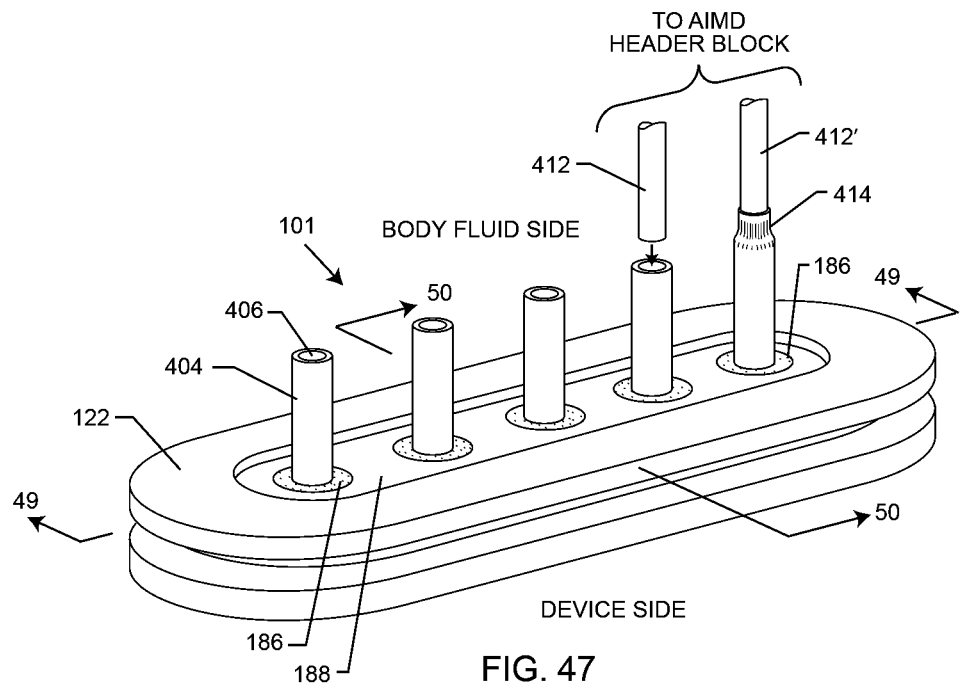
FIG. 47 is similar to FIG. 36 except that now the conductive inserts are in the form of hollow tubelets.

FIG. 47 is similar to FIG. 38 except that the conductive inserts 404 are in the form of hollow tubelets. Again, like all of the conductive inserts of the present invention, these are co-fired with the conductive paste 186 and the alumina insulator 188. The crimp posts 404 extend to the body fluid side to receive wires coming from an AIMD header block or from an AIMD implanted lead 412. As shown, the lead conductor 412 is inserted inside the crimp post opening 406 and then a crimp 414 is formed as shown, which makes a solid electrical and mechanical connection. This also can be backed up with a laser weld (not shown) to effect a metallurgical connection as well.

Figure 48:
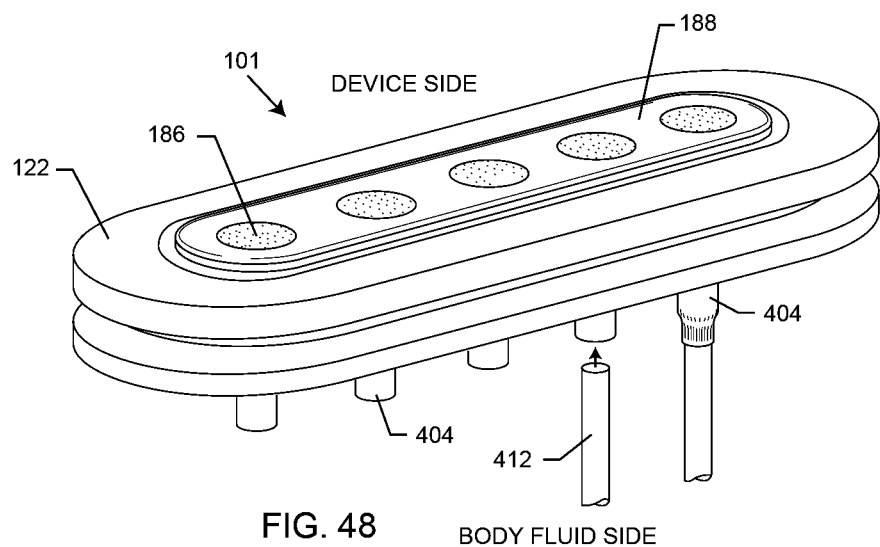
FIG. 48 shows the hermetic terminal assembly of FIG. 47 now with a crimp post inverted so one can see the device side on top.
Figure 49:
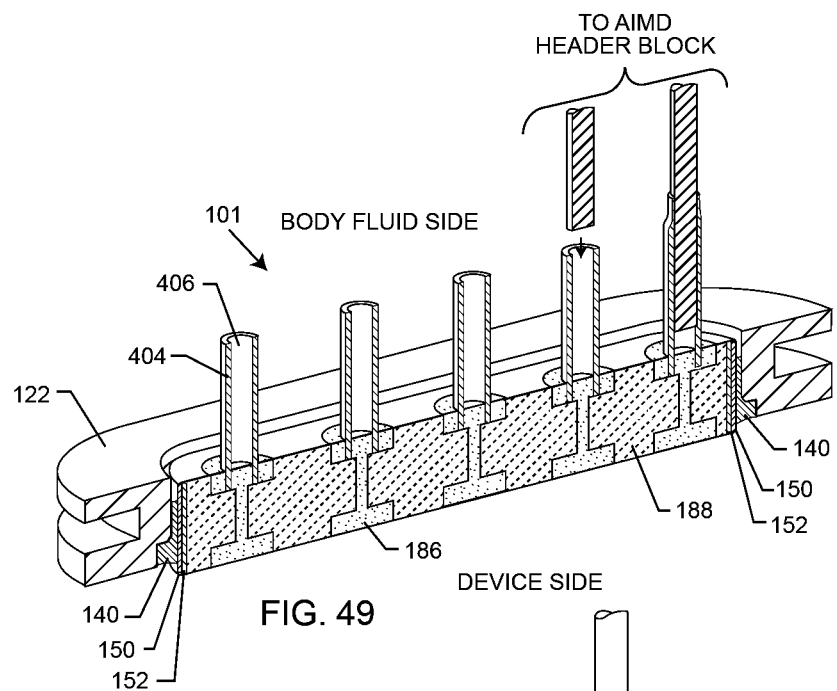
FIG. 49 is a sectional view taken generally from section 49-49 from FIG. 47.
Figure 50:
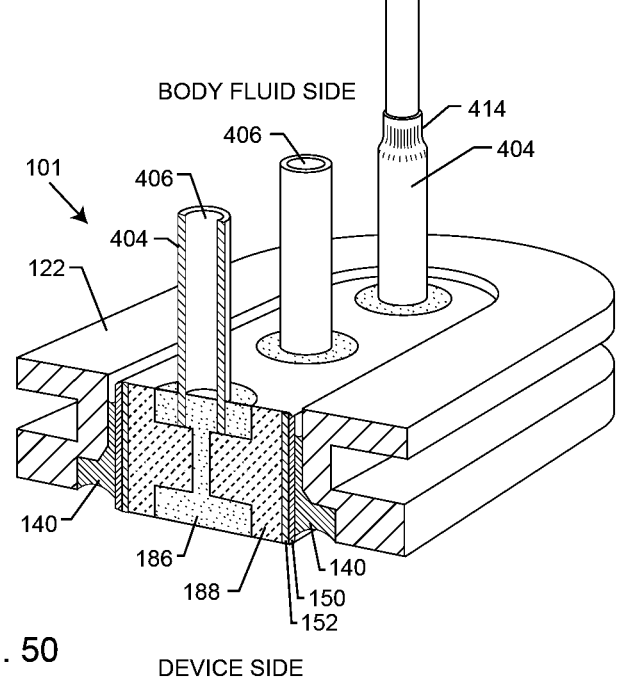
FIG. 50 is a sectional view taken generally from section 50-50 from FIG. 47.

FIG. 48 shows the hermetic terminal assembly with a crimp post 404 inverted so one can see the device side. In this case, the crimp post only partially fills the via hole with the conductive fill. In other words, it does not go all the way through from the device side to the body fluid side. This feature is best shown in FIGS. 49 and 50, which is taken from section 49-49 and 50-50 from FIG. 47. In this case, one can see that the top and bottom of the conductive fill via 186 has been enlarged with a counterbore to increase the contact surface area and also to provide an area for co-firing of the crimp post 404 which has a hollow center 406. It is desirable that the conductive fill is shown mechanically and electrically attached to both the outside diameter 404 and the inside diameter 404 of the tube, such that suitable pull strength is achieved.

FIG. 50 is generally taken from section 50-50 from FIG. 47 and shows a cross-section right through the center line of the hermetic seal assembly. One can see the cross-section of the crimp tube 406 solidly embedded in the conductive fill material 186 as shown.

Figure 51:
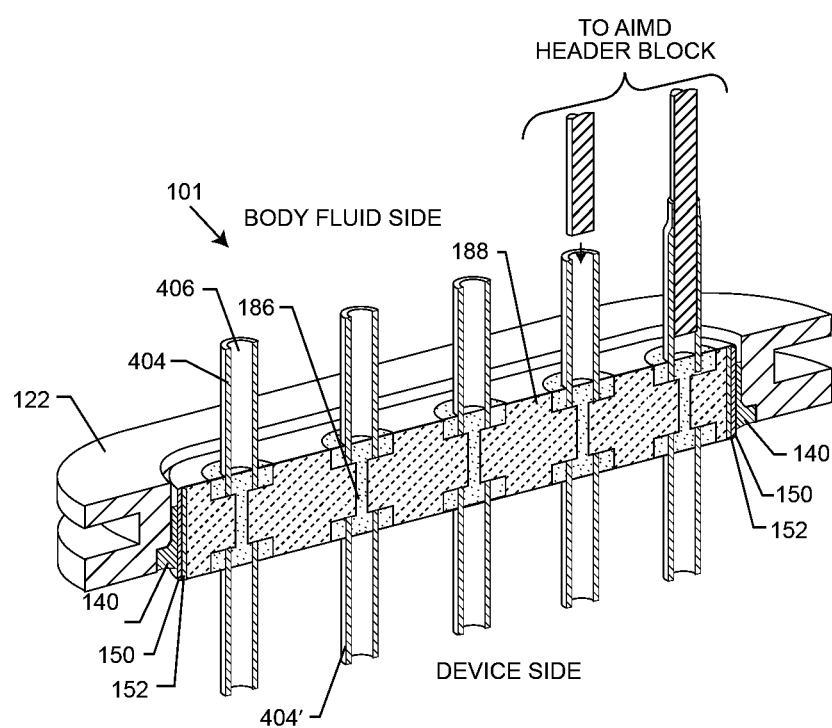
FIG. 51 is very similar to FIG. 49 except in this case, there are crimp posts positioned on both the body fluid side and the device side.

FIG. 51 is very similar to FIG. 49 except in this case, there are crimp posts 404 and 404' positioned on both the body fluid side and the device side. In this way, body fluid side attachments could be made to leadwires or lead conductors and electrical circuit connections can be made to electronic circuits (not shown) inside of the AIMD housing. Referring once again to FIG. 51, one can see that on the body fluid side that the crimp post 404 would have to be of non-toxic and biocompatible materials, such as platinum and the like. However, on the device side, for example, where crimp post 404' is shown, these could be inexpensive and non-biocompatible materials, such as copper since they are not exposed to body fluids. Referring once again to FIG. 51, the conductive fill material 186 has a lower conductivity in comparison to the solid metal crimp post material 406. The long and relatively narrow section of the conductive fill via that's between the top and bottom counterbores therefore, is relatively undesirable since it will create resistance through the via from the body fluid side to the device side.

Figure 52:
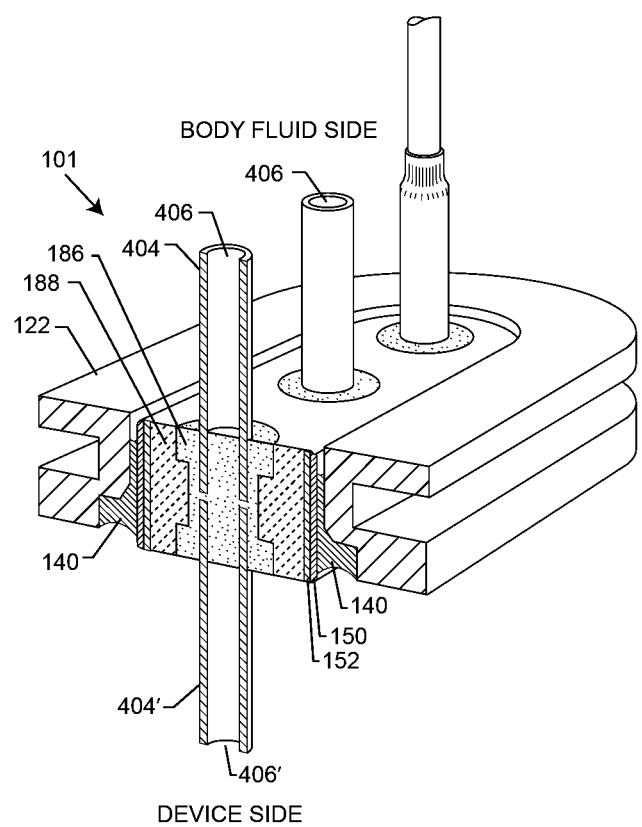
FIG. 52 is very similar to FIG. 50, now with a crimp post on both the body fluid side and the device side.

Another embodiment is shown in FIG. 52, wherein one can see that the crimp post 404 passes through a larger diameter conductive fill via 186. In addition, the top crimp post 404 comes very close to touching the bottom crimp post 404'. In this case, the electrical conductivity from the body fluid side to the device side is greatly reduced. An optional configuration is shown in FIG. 27 wherein, the crimp post or tube is continuous from top to bottom thereby affecting the lowest resistivity possible.

Figure 53:
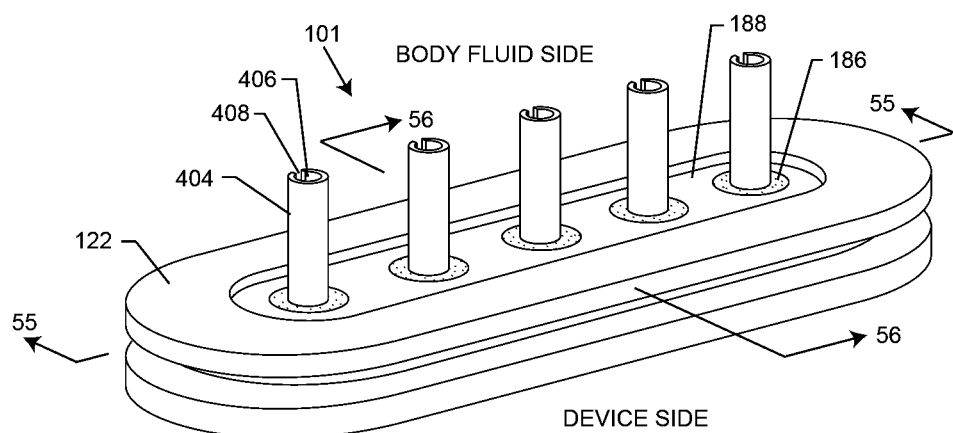
FIG. 53 is very similar to FIG. 52 except in this case, there is a slit along the edge of the crimp post.

FIG. 53 is very similar to FIG. 52 except in this case, there is a slit/slot 408 along the edge of the crimp post 404 which allows it to be easily crushed down onto a leadwire (not shown).

Figure 54:
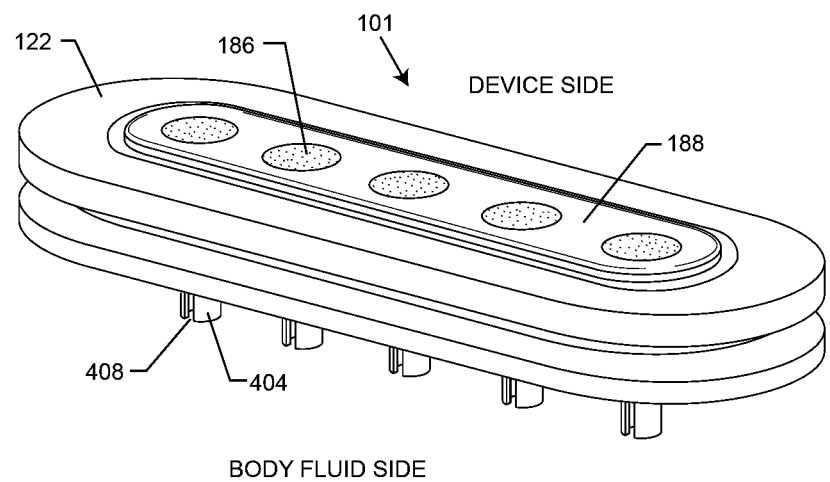
FIG. 54 shows the hermetic seal with the slotted crimp post of FIG. 53 inverted.

FIG. 54 shows the hermetic seal with the slotted crimp post of FIG. 53 inverted.

Figure 55:
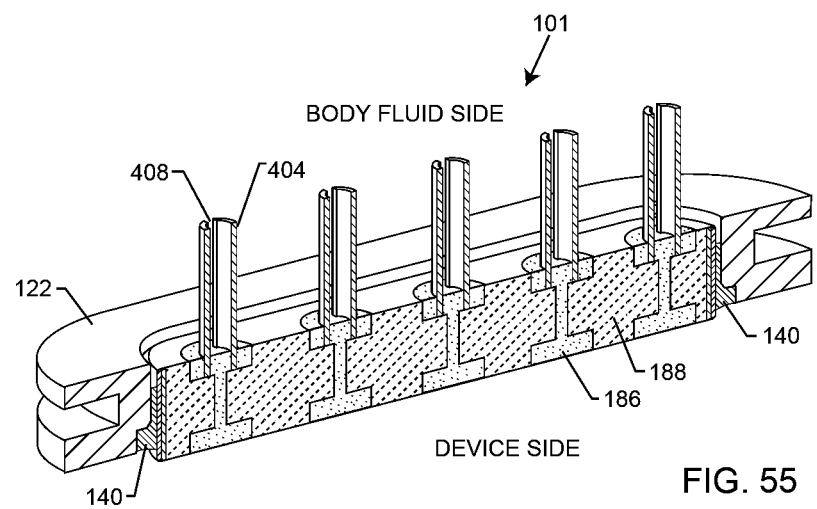
FIG. 55 is taken from section 55-55 from FIG. 53 showing the slotted crimp post in side view.

FIG. 55 is taken from section 55-55 from FIG. 53 showing the slotted crimp post in side view.

Figure 56:
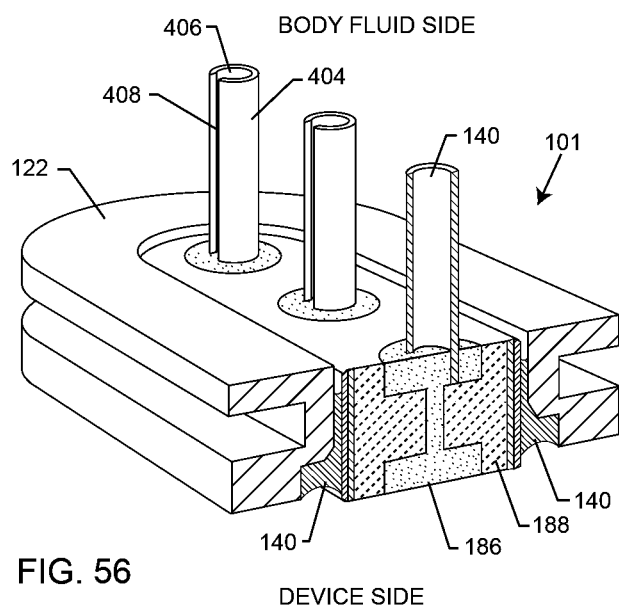
FIG. 56 is taken from section 56-56 from FIG. 53 again showing the slotted crimp post.

FIG. 56 is taken from section 56-56 from FIG. 53 again showing the slotted 408 crimp post 404.

Figure 57:
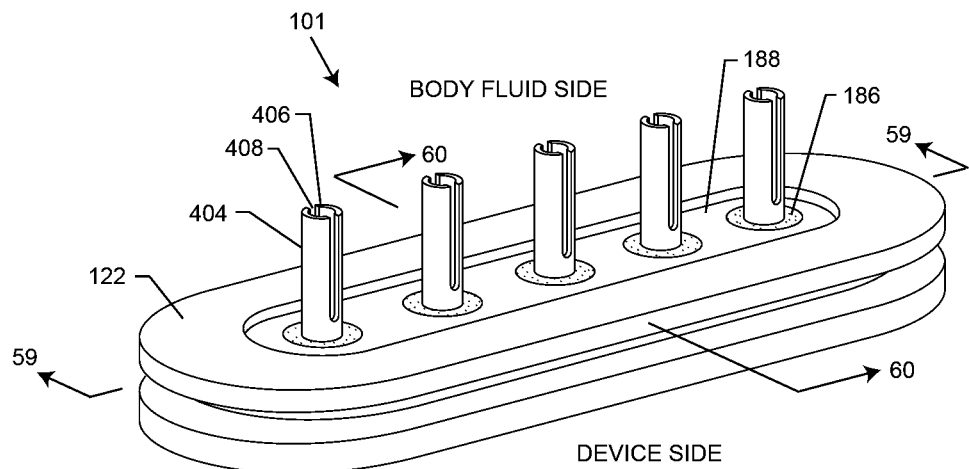
FIG. 57 is very similar to FIG. 53 except that the crimp post has double slots.

FIG. 57 is very similar to FIG. 53 except that the crimp post 404 has double slots 408 as shown. Again, this would be to facilitate crimping or crushing down the tube of a smaller diameter lead conductor (not shown) that would be inserted into the inner diameter 406.

Figure 58:
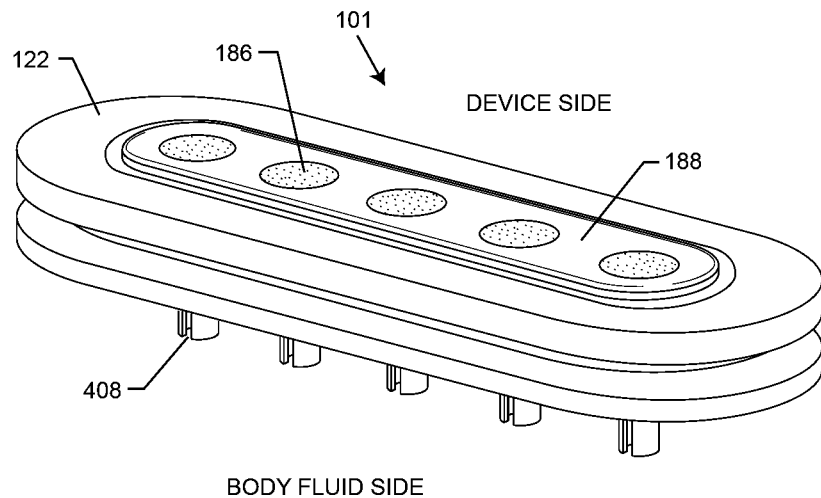
FIG. 58 is the inverted view of the structure from FIG. 57.

FIG. 58 is the inverted view taken from FIG. 57.

Figure 59:
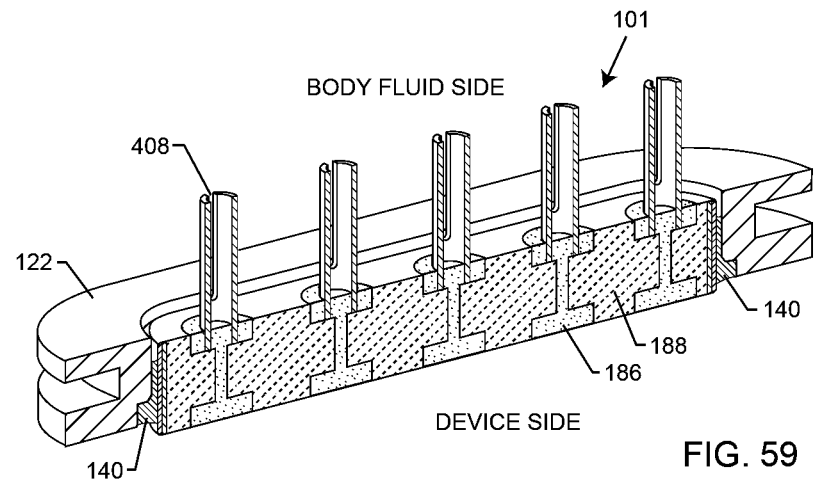
FIG. 59 is taken from section 59-59 from FIG. 57 showing the double slotted crimp post in half section.

FIG. 59 is taken from section 59-59 from FIG. 57 showing the double slotted crimp post 404 in half section.

Figure 60:
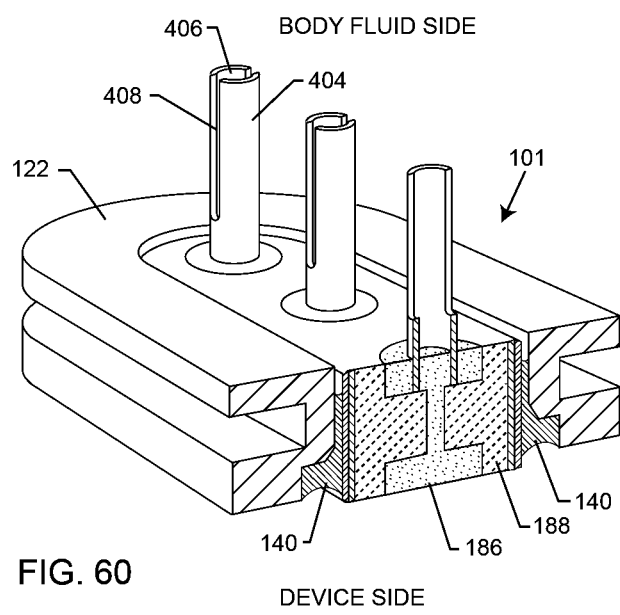
FIG. 60 is taken from section 60-60 from FIG. 57 right through the center of the device, this time going through the center of both slots.

FIG. 60 is taken from section 60-60 from FIG. 57 right through the center of the device, this time going through the center of both slots 408.

FIGS. 61 and 61A through 65 and 65A show alternative configurations for either partial or fully through crimp posts.

Figure 66:
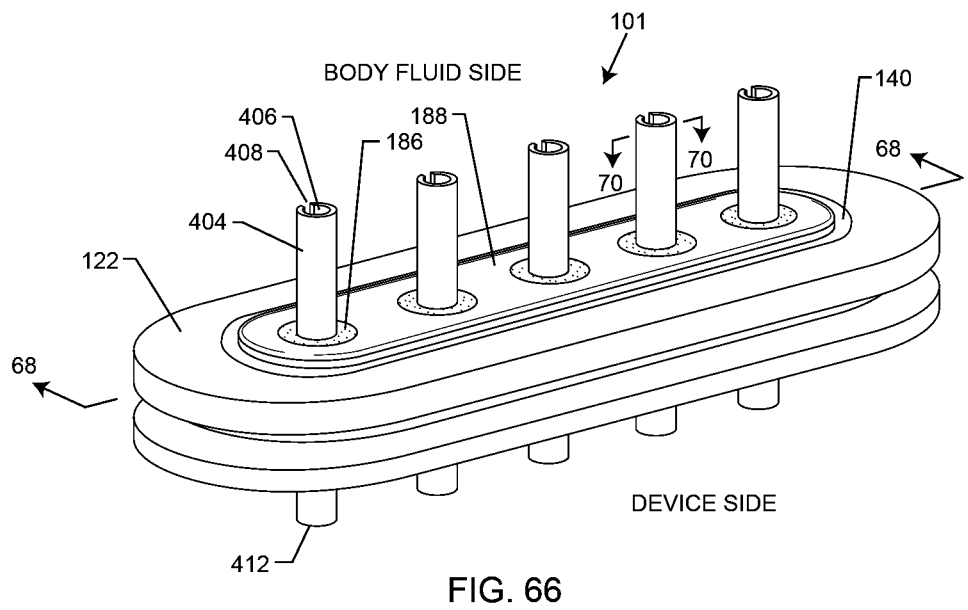
FIG. 66 shows an embodiment of a hermetical terminal assembly which has a single slot in the crimp post.

FIG. 66 has a single slot 408 in the crimp post 404. This is very similar to FIG. 47 except that the crimp post 404 is continuous all the way through the via from the body fluid side to the device side.

Figure 67:
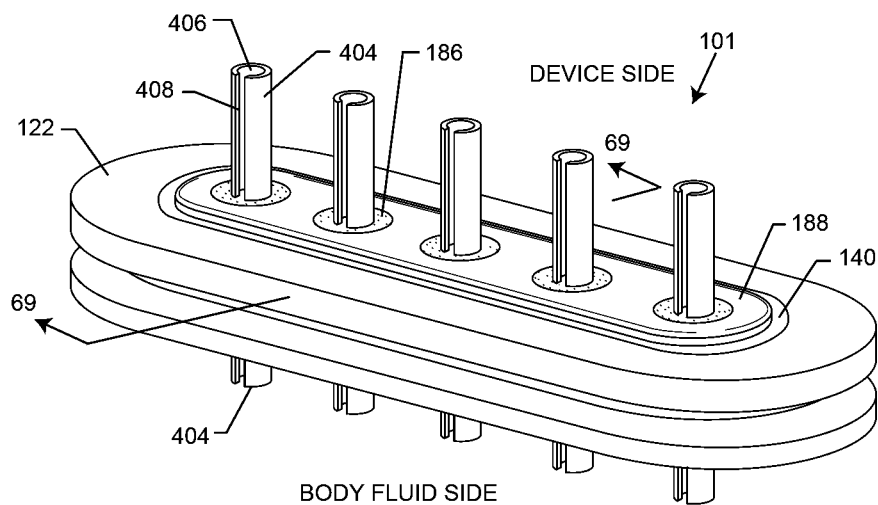
FIG. 67 shows the perspective view of FIG. 66 inverted so one can see the device side.

FIG. 67 shows the perspective view of FIG. 66 inverted so one can see the device side. In this case, there is a single slot 408 shown. It will be understood by those skilled in the art that this could be a double slot or even multiple slots to achieve optimal crimping.

Figure 68:
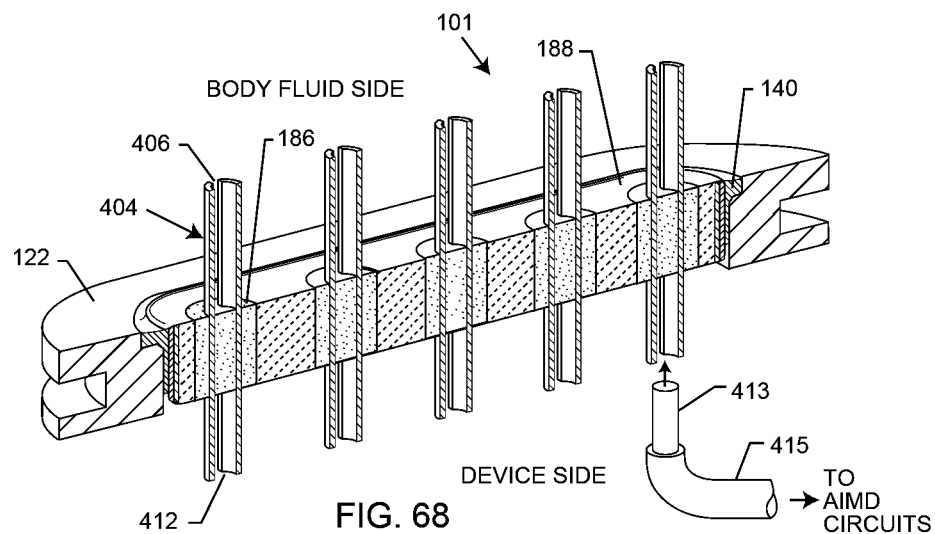
FIG. 68 is taken from section 68-68 from FIG. 66 illustrating that the slotted crimp post extending all the way through the conductive filled via from the body fluid side to the device side.

FIG. 68 is taken from section 68-68 from FIG. 66 illustrating that the slotted crimp post 404 extends all the way through the conductive filled via from the body fluid side to the device side. An advantage to this type of arrangement is that very inexpensive wires can then be used on the device side. For example, commercially available insulated 415 copper wires 413 can be crimped 412 on the device side and routed to convenient circuit board locations. This is far less expensive than running, for example, platinum wiring inside of a device. Again, inside of a device, noble materials and biocompatibility are not required since there is no exposure to body fluid or tissues.

Figure 69:
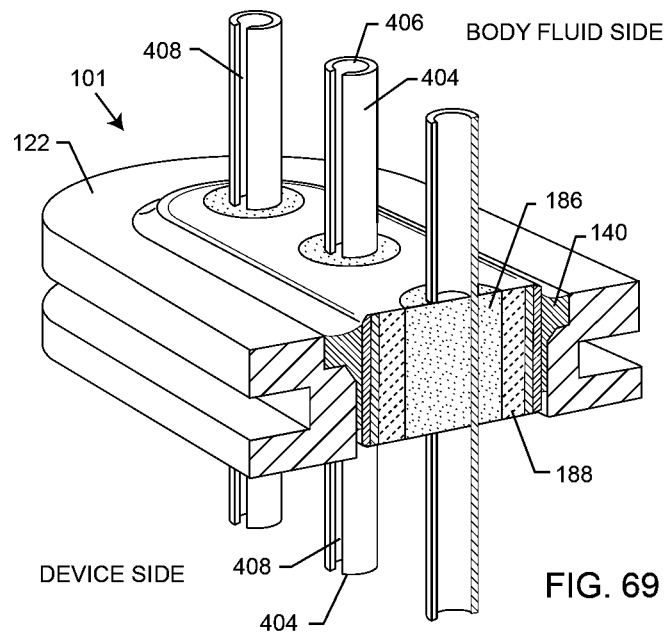
FIG. 69 is taken from section 69-69 from FIG. 67 again, illustrating how the conductive fill penetrates both the outside and the inside diameter of the crimp post.

FIG. 69 is taken from section 69-69 from FIG. 67, again illustrating how the conductive fill 186 penetrates both the outside and the inside diameter of the crimp post 404. This gives the crimp post 404 a great deal of mechanical strength particularly in pull or sheer test.

Figure 70A:
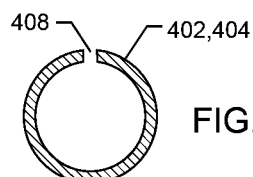
FIG. 70A shows a sectional view through one embodiment of a crimp post with one slot.
Figure 70B:
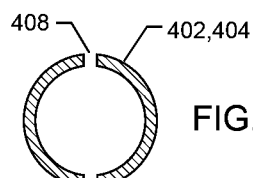
FIG. 70B shows a sectional view through another embodiment of a crimp post with two halves.
Figure 70C:
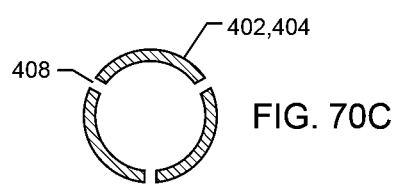
FIG. 70C shows a sectional view through another embodiment of a crimp post with three sections.
Figure 70D:
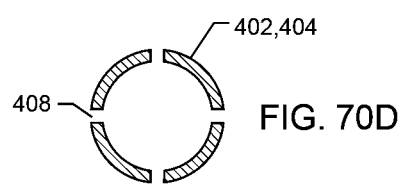
FIG. 70D shows a sectional view through another embodiment of a crimp post with four sections.
Figure 70E:
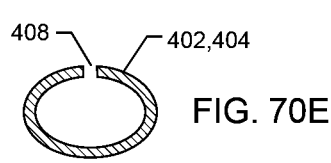
FIG. 70E shows a sectional view through another embodiment of an oval crimp post with one slot.
Figure 70F:
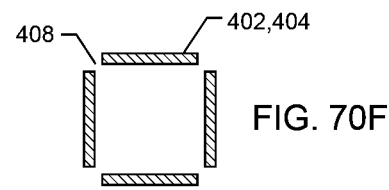
FIG. 70F shows a sectional view through another embodiment of a square crimp post having four parts.

FIGS. 70A through 70F illustrate different top views for the crimp post arrangements previously described. FIG. 70A is a top view of a single slotted 408 crimp post 404. FIG. 70B is a top view of a double slotted 404 crimp post. FIG. 70B could also be formed from two completely separate semi-circular pieces of solid metal which are then co-fired into the conductive fill to form the crimp post structure. FIG. 70C illustrates that three separate pieces could be used resulting in three slots 408. FIG. 70D is very similar to FIG. 70C except that in this case, there are four pieces. FIG. 70E illustrates a single slot oval shaped through crimp post whereas, FIG. 70F illustrates that it could take on any other shape, such as square, rectangular or the like.

Figure 71:
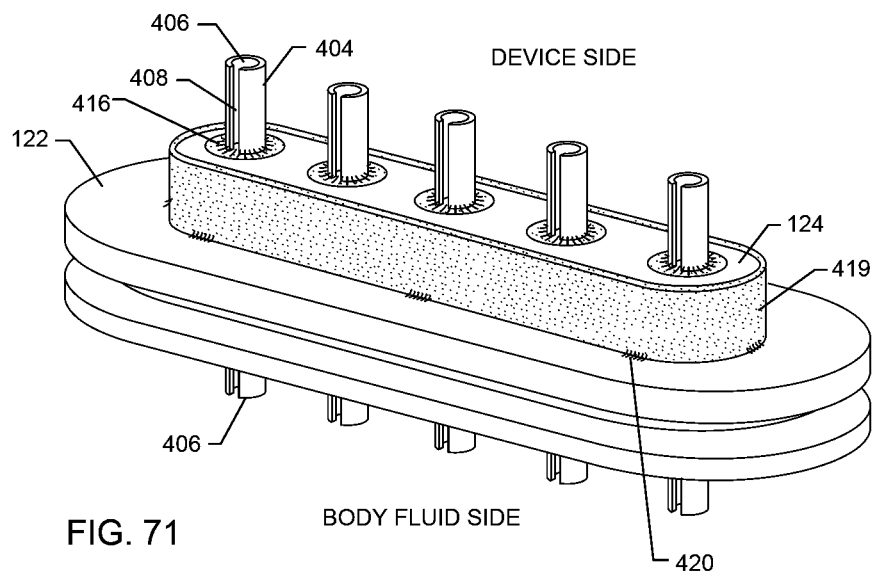
FIG. 71 illustrates that any of the novel hermetic seals of the present invention can have a device side mounted feedthrough capacitor.

FIG. 71 illustrates that any of the novel hermetic seals of the present invention can have a mounted feedthrough capacitor 124. In this case, an electrical connection 416 is made from each of the feedthrough capacitor center holes to each individual crimp post 404, which could be a solder, thermal-setting conductive adhesive or the like. There is also a suitable electrical connection made from the capacitor outside perimeter metallization 419 to the ferrule 122. The electrical connection material 420 could be continuous or discontinuous as shown. In a preferred embodiment, the electrical connection 420 would be between the capacitor outside perimeter ground metallization 419 into gold brazed areas on the hermetic seal ferrule 122, such that no oxides of titanium could build up in the electrical connection which could preclude proper high frequency attenuation of the filter.

Figure 72:
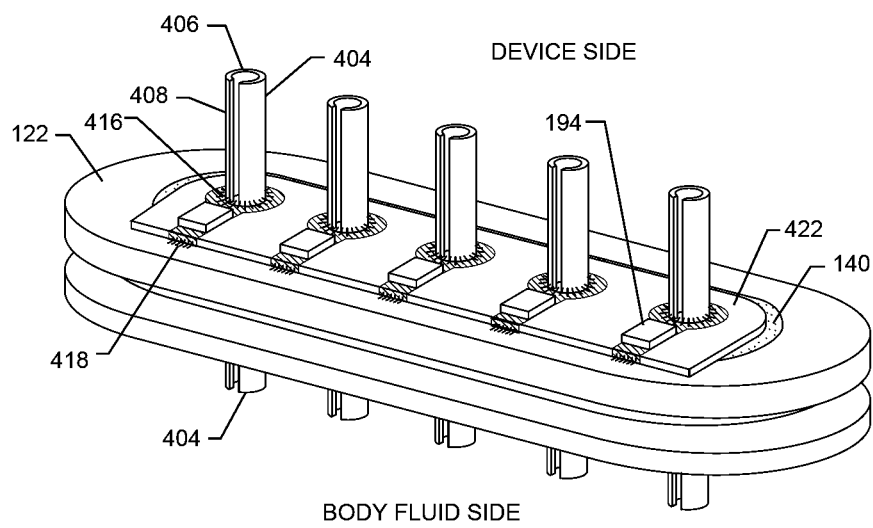
FIG. 72 illustrates an alternative filter embodiment in comparison to FIG. 71, wherein a circuit substrate has been placed over the five crimp posts with individual MLCC chip capacitors.

FIG. 72 illustrates an alternative filter embodiment wherein, a circuit substrate 422 has been placed over the five crimp posts 404. There are five individual MLCC chip capacitors 194, which are mounted to circuit traces that are already pre-printed on the circuit board 422. Again, an electrical connection would be made from the circuit board via hole end to each of the crimp posts 404. In addition, the capacitors would all be connected to a ground circuit trace 418 or individually grounded to a gold braze area as shown.

Although several embodiments have been described in detail for purposes of illustration, various modifications may be made to each without departing from the scope and spirit of the invention. Accordingly, the invention is not to be limited, except as by the appended claims.

What is claimed is:

1. A hermetically sealed feedthrough for attachment to an active implantable medical device (AIMD), the feedthrough comprising:
   a) a dielectric substrate hermetically sealed to a ferrule by a gold braze;
   b) a via hole disposed through the dielectric substrate from a first side to a second side;
   c) a conductive sintered paste fill disposed within the via hole forming a filled via electrically conductive between the first side and the second side; and
   d) a conductive solid metallic insert at least partially disposed within the conductive sintered paste fill;
   e) wherein the conductive sintered paste fill and the conductive solid metallic insert are co-fired with the dielectric substrate forming a hermetically sealed and electrically conductive pathway through the dielectric substrate between the first side and the second side.

2. The feedthrough of claim 1, wherein the conductive fill comprises a metallic fill.

3. The feedthrough of claim 1, wherein an inherent shrink rate during a co-firing treatment of the insulator in a green state is greater than that of an inherent shrink rate during the co-firing treatment of the metallic fill in a green state.

4. The feedthrough of claim 1, wherein first and second ends of the insert are substantially flush with the respective first side and second side of the dielectric substrate.

5. The feedthrough of claim 1, wherein at least one of an insert first end and an second insert end extends outwardly beyond a respective one of the first side and second side of the dielectric substrate.

6. The feedthrough of claim 5, wherein the insert comprises an enlarged end cap at least one of its insert first and second ends.

7. A hermetically sealed feedthrough for attachment to an active implantable medical device (AIMD), the feedthrough comprising:
- a) a conductive ferrule comprising a ferrule sidewall having an inner ferrule surface defining a ferrule opening, wherein the ferrule sidewall extends from a ferrule first end surface to a ferrule second end surface, and wherein the ferrule is configured to be attachable to an opening in a housing of an active implantable medical device;
- b) an insulator residing at least partially within the inner ferrule surface, wherein the insulator comprises an outer insulator surface extending from an insulator first end surface disposed adjacent to the ferrule first end surface to an opposed insulator second end surface disposed adjacent to the ferrule second end surface;
- c) a first metallization contacting at least a portion of the outer surface of the insulator;
- d) an electrically conductive material hermetically sealing the ferrule sidewall to the first metallization contacting the outer surface of the insulator;
- e) at least one via hole extending through the insulator from the insulator first end surface to the insulator second end surface;
- f) an electrically conductive insert residing in the via hole and comprising an insert sidewall extending from an insert first end to an insert second end, wherein the insert first end is disposed at or adjacent to the insulator first end surface and the insert second end is disposed at or adjacent to the insulator second end surface; and
- g) a conductive fill residing in the at least one via hole in contact with the insert sidewall, the conductive fill extending from a conductive fill first end disposed at or adjacent to the insulator first end surface to a conductive fill second end disposed at or adjacent to the insulator second end surface,
- h) wherein the conductive fill is in a hermetically sealed relationship with both the insulator at the at least one via hole and the insert sidewall so that the conductive insert provides an electrically conductive pathway extending through the insulator to or adjacent to the insulator first end surface and to or adjacent to the insulator second end surface.

8. The feedthrough of claim 7, wherein the conductive fill comprises a metallic fill.

9. The feedthrough of claim 8, wherein the conductive insert comprises a metallic insert, and where the metallic insert and the metallic fill are of the same metallic material.

10. The feedthrough of claim 8, wherein an inherent shrink rate during a co-firing treatment of the insulator in a green state is greater than that of an inherent shrink rate during the co-firing treatment of the metallic fill in a green state.

11. The feedthrough of claim 7, wherein the conductive fill comprises a platinum fill.

12. The feedthrough of claim 11, wherein the conductive insert comprises a platinum insert.

13. The feedthrough of claim 12, wherein the insulator comprises an alumina ceramic substrate comprised of at least 96 percent alumina.

14. The feedthrough of claim 7, wherein the conductive fill is a platinum fill that forms a first tortuous and mutually conformal knitline with the insulator at the at least one via hole.

15. The feedthrough of claim 7, wherein the conductive fill is a platinum fill that forms a second tortuous and mutually conformal knitline with the insert sidewall, the insert being a platinum insert.

16. The feedthrough of claim 7, wherein the conductive fill does not contact:
- i) the insert first end disposed at or adjacent to the insulator first end surface, and
- ii) the insert second end disposed at or adjacent to the insulator second end surface.

17. The feedthrough of claim 7, wherein the insert first and second ends are substantially flush with the respective insulator first and second end surfaces.

18. The feedthrough of claim 7, wherein at least one of the insert first and second ends extends outwardly beyond a respective one of the insulator first and second end surfaces.

19. The feedthrough of claim 18, wherein the insert comprises an enlarged end cap at at least one of its insert first and second ends.

20. The feedthrough of claim 7, wherein the conductive insert comprises a first insert portion separate and distinct from a second insert portion, and wherein the first and second insert portions are adjacent to or abut one another at an intermediate location along a length of the at least one via hole in which the insert resides.

21. The feedthrough of claim 7, wherein the conductive insert comprises a crimp post portion extending outwardly beyond at least one of the insulator first and second end surfaces.

22. The feedthrough of claim 21, wherein the crimp post portion comprises a receptacle configured to receive a conductive wire, and wherein the crimp post portion comprises a cross-sectional shape selected from the group consisting of a circle, an oval, a rectangle, and a square.

23. The feedthrough of claim 22, wherein the receptacle of the crimp post portion of the conductive insert is disposed perpendicular to a longitudinal length of the crimp post portion.

24. The feedthrough of claim 22, wherein the receptacle of the crimp post portion of the conductive insert is aligned along a longitudinal length of the crimp post portion.

25. The feedthrough of claim 22, wherein the crimp post portion of the conductive insert comprises at least one slot that is at least partially disposed along a longitudinal length of the crimp post portion.

26. The feedthrough of claim 7, wherein the conductive insert has a length extending from the insert first end to the insert second end and wherein at least one slot extends along the length of the conductive insert from the insert first end to the insert second end.

27. The feedthrough of claim 7, wherein the conductive insert is selected from the group consisting of titanium, platinum, platinum-iridium alloys, tantalum, niobium, zirconium, hafnium, nitinol, Co—Cr—Ni alloys, stainless steel, gold, gold alloys, ZrC, ZrN, TiN, NbO, TiC, TaC, and combinations thereof.

28. The feedthrough of claim 7, wherein the at least one via hole has a via hole length extending from the insulator first end surface to the insulator second end surface, and wherein the conductive insert has a larger cross-sectional area at or adjacent to at least one of the insulator first and second end surfaces than at an intermediate location along the via hole length between the insulator first and second end surfaces.

29. The feedthrough of claim 7, wherein the insulator first end surface is one of a body fluid side and a device side, and the insulator second end surface is the other of the body fluid side and the device side.

30. The feedthrough of claim 7, wherein the conductive insert is a drawn filled tube comprising a silver core provided with an MP35N cladding.

31. The feedthrough of claim 7, wherein the conductive fill and the conductive insert are characterized as having been co-fired with the insulator to thereby form a hermetically sealed and electrically conductive pathway from the insulator first end surface to the insulator second end surface.

32. The feedthrough of claim 7, wherein both of the insert first and second ends extend axially outwardly beyond the respective conductive fill first and second ends.

33. A hermetically sealed feedthrough assembly for attachment to an active implantable medical device (AIMD), the feedthrough comprising:
a) a feedthrough, comprising:
  i) conductive ferrule comprising a ferrule sidewall having an inner ferrule surface defining a ferrule opening, wherein the ferrule sidewall extends from a ferrule first end surface to a ferrule second end surface, and wherein the ferrule is configured to be attachable to an opening in a housing of an active implantable medical device;
  ii) an alumina insulator residing at least partially within the inner ferrule surface, wherein the insulator comprises an outer insulator surface extending from an insulator first end surface disposed adjacent to the ferrule first end surface to an opposed insulator second end surface disposed adjacent to the ferrule second end surface;
  iii) a first metallization contacting at least a portion of the outer surface of the insulator;
  iv) a first electrically conductive material hermetically sealing the ferrule sidewall to the first metallization contacting the outer surface of the insulator;
  v) at least one via hole extending through the alumina insulator from the insulator first end surface to the insulator second end surface;
  vi) a platinum insert residing in the via hole and comprising an insert sidewall extending from a insert first end to an insert second end, wherein at least the insert first end extends outwardly beyond the insulator first end surface and the insert second end is disposed at or adjacent to the insulator second end surface; and
  vii) a platinum fill residing in the at least one via hole in contact with the platinum insert sidewall, the platinum fill extending from a platinum fill first end disposed at or adjacent to the insulator first end surface to a platinum fill second end disposed at or adjacent to the insulator second end surface,
  viii) wherein the platinum fill is in a hermetically sealed relationship with both the insulator at the at least one via hole and the platinum insert sidewall so that the platinum insert provides an electrically conductive pathway extending through the alumina insulator to or adjacent to the insulator first end surface and to or adjacent to the insulator second end surface;

b) a feedthrough capacitor, comprising:
  i) a capacitor dielectric body;
  ii) at least one active electrode plate and at least one ground electrode plate supported in the capacitor dielectric body in spaced relation with each other;
  iii) at least one open bore formed axially through the capacitor dielectric body;
  iv) a second metallization contacting the bore in conductive relation with the active electrode plate; and
  v) a third metallization contacting an outer surface of the capacitor dielectric body in conductive relation with the ground electrode plate;
c) a second electrically conductive material physically contacting and electrically coupling the second metallization in the open bore of the capacitor dielectric body to the insert second end at or adjacent to the insulator second end surface to thereby electrically connect the at least one active electrode plate to the conductive insert, wherein the opposed insert first end extends outwardly beyond the insulator first end surface; and
d) a third electrically conductive material physically contacting and electrically coupling the third metallization to the conductive ferrule.

34. The feedthrough assembly of claim 33, wherein the insert second end extends outwardly beyond the insert second end surface.

35. A hermetically sealed feedthrough assembly for attachment to an active implantable medical device (AIMD), the feedthrough comprising:
a) a feedthrough, comprising:
  i) conductive ferrule comprising a ferrule sidewall having an inner ferrule surface defining a ferrule opening, wherein the ferrule sidewall extends from a ferrule first end surface to a ferrule second end surface, and wherein the ferrule is configured to be attachable to an opening in a housing of an active implantable medical device;
  ii) an alumina insulator residing at least partially within the inner ferrule surface, wherein the insulator comprises an outer insulator surface extending from an insulator first end surface disposed adjacent to the ferrule first end surface to an opposed insulator second end surface disposed adjacent to the ferrule second end surface;
  iii) a first metallization contacting at least a portion of the outer surface of the insulator;
  iv) an electrically conductive material hermetically sealing the ferrule sidewall to the first metallization contacting the outer surface of the insulator;
  v) at least one via hole extending through the alumina insulator from the insulator first end surface to the insulator second end surface;
  vi) a platinum insert residing in the via hole and comprising an insert sidewall extending from an insert first end to an insert second end, wherein at least the insert first end extends outwardly beyond the insulator first end surface and the insert second end is disposed at or adjacent to the insulator second end surface; and
  vii) a platinum fill residing in the at least one via hole in contact with the platinum insert sidewall, the platinum fill extending from a platinum fill first end disposed at or adjacent to the insulator first end surface to a platinum fill second end disposed at or adjacent to the insulator second end surface,
  viii) wherein the platinum fill is in a hermetically sealed relationship with both the insulator at the at least one via hole and the platinum insert sidewall so that the platinum insert provides as electrically conductive pathway extending through the alumina insulator to or adjacent to the insulator first end surface and to or adjacent to the insulator second end surface;

b) at least one monolithic chip capacitor disposed adjacent to the circuit board substrate, wherein the chip capacitor comprises:
  i) a chip capacitor dielectric supporting at least one active chip electrode plate interleaved in a capacitive relationship with at least one ground chip electrode plate;
  ii) a chip active metallization electrically connected to the at least one active chip electrode plate at an active end of the chip capacitor dielectric, and a chip ground metallization electrically connected to the at least one ground chip electrode plate at a ground end of the chip capacitor dielectric, wherein the active end is spaced from the ground end of the chip capacitor dielectric; and c) a first electrically conductive material physically contacting and electrically coupling the chip active metallization to the insert first end extending outwardly beyond the insulator first end surface to thereby electrically connect the at least one chip electrode plate to the platinum insert; and d) a second electrically conductive material physically contacting and electrically coupling the chip ground metallization to the ferrule.

36. A hermetically sealed feedthrough for attachment to an active implantable medical device (AIMD), the feedthrough comprising:
  a) a conductive ferrule comprising a ferrule sidewall having an inner ferrule surface defining a ferrule opening, wherein the ferrule sidewall extends from a ferrule first end surface to a ferrule second end surface, and wherein the ferrule is configured to be attachable to an opening in a housing of an active implantable medical device;
  b) an insulator residing at least partially within the inner ferrule surface, wherein the insulator comprises an outer insulator surface extending from insulator first end surface disposed adjacent to the ferrule first end surface to an opposed insulator second end surface disposed adjacent to the ferrule second end surface;
  c) a first metallization contacting at least a portion of the outer surface of the insulator;
  d) an electrically conductive material hermetically sealing the ferrule sidewall to the first metallization contacting the outer surface of the insulator;
  e) at least one via hole extending through the insulator from the insulator first end surface to the insulator second end surface;
  f) an electrically conductive insert extending along a longitudinal axis in the via hole, the insert comprising an insert sidewall spaced from the longitudinal axis and extending from an insert first end to an insert second end, wherein the insert first end is disposed at or adjacent to the insulator first end surface and the insert second end is disposed at or adjacent to the second insulator second end surface; and
  g) a conductive fill residing in the at least one via hole in contact with the insert sidewall, the conductive fill being spaced from the longitudinal axis of the conductive insert and extending from a conductive fill first end disposed at or adjacent to the insulator first end surface to a conductive fill second end disposed at or adjacent to the insulator second end surface,
  h) wherein the conductive fill is in a hermetically sealed relationship with both the insulator at the at least one via hole and the insert sidewall so that the conductive insert provides an electrically conductive pathway extending through the insulator to or adjacent to the insulator first end surface and to or adjacent to the insulator second end surface.

* * * * *

UNITED STATES PATENT AND TRADEMARK OFFICE
CERTIFICATE OF CORRECTION

PATENT NO. : 9,889,306 B2
APPLICATION NO. : 14/797123
DATED : February 13, 2018
INVENTOR(S) : Robert A. Stevenson et al.

Page 1 of 1

It is certified that error appears in the above-identified patent and that said Letters Patent is hereby corrected as shown below:

In the Claims

Column 29, Line 2 (Claim 5, Line 2) delete "second insert" and insert --insert second--

Column 31, Line 49 (Claim 33, Line 28) delete "a" and insert --an--

Column 33, Line 23 (Claim 35, Line 66) after the word "chip" insert --active--

Column 34, Line 3 (Claim 36, Line 12) after the word "from" insert --an--

Signed and Sealed this
Fifteenth Day of May, 2018

Andrei Iancu
*Director of the United States Patent and Trademark Office*